(12) United States Patent
Krarup

(10) Patent No.: US 7,897,734 B2
(45) Date of Patent: Mar. 1, 2011

(54) METHOD FOR THE PRODUCTION OF PROTEINS

(75) Inventor: Janus Krarup, Gentofte (DK)

(73) Assignee: Novo Nordisk Healthcare AG, Zurich (CH)

( * ) Notice: Subject to any disclaimer, the term of this patent is extended or adjusted under 35 U.S.C. 154(b) by 667 days.

(21) Appl. No.: 11/229,428

(22) Filed: Sep. 15, 2005

(65) Prior Publication Data
US 2006/0051854 A1    Mar. 9, 2006

Related U.S. Application Data

(63) Continuation of application No. PCT/DK2004/000183, filed on Mar. 18, 2004.

(60) Provisional application No. 60/457,809, filed on Mar. 26, 2003.

(51) Int. Cl.
*A23J 1/00* (2006.01)
(52) U.S. Cl. ........................................................ 530/412
(58) Field of Classification Search .................... 530/412
See application file for complete search history.

(56) References Cited

U.S. PATENT DOCUMENTS

| | | | |
|---|---|---|---|
| 4,297,344 A | 10/1981 | Schwinn et al. |
| 4,382,083 A | 5/1983 | Thomas |
| 4,404,132 A | 9/1983 | Mitra |
| 4,495,278 A | 1/1985 | Thomas |
| 4,784,950 A | 11/1988 | Hagen et al. |
| 4,956,386 A | 9/1990 | McLoughlin et al. |
| 5,180,583 A | 1/1993 | Hedner |
| 5,288,629 A | 2/1994 | Berkner |
| 5,399,670 A | 3/1995 | Bhattacharya et al. |
| 5,457,181 A | 10/1995 | Michalski et al. |
| 5,576,291 A | 11/1996 | Curtis et al. |
| 5,649,959 A | 7/1997 | Hannam et al. |
| 5,700,914 A | 12/1997 | Jorgensen |
| 5,750,358 A | 5/1998 | Morrissey |
| 5,770,700 A | 6/1998 | Webb et al. |
| 5,804,420 A | 9/1998 | Chan |
| 5,817,788 A | 10/1998 | Berkner et al. |
| 5,824,780 A | 10/1998 | Curtis et al. |
| 5,830,852 A | 11/1998 | Thatcher et al. |
| 5,831,026 A | 11/1998 | Almstedt et al. |
| 5,833,982 A | 11/1998 | Berkner et al. |
| 5,925,738 A | 7/1999 | Miekka et al. |
| 5,925,739 A | 7/1999 | Spira et al. |
| 5,962,650 A | 10/1999 | Osterberg et al. |
| 5,993,795 A | 11/1999 | Osawa et al. |
| 6,034,222 A | 3/2000 | Fischer et al. |
| 6,183,743 B1 | 2/2001 | Hart et al. |
| 6,228,620 B1 | 5/2001 | Chapman et al. |
| 6,277,828 B1 | 8/2001 | Knepp et al. |
| 6,310,183 B1 | 10/2001 | Johannessen et al. |
| 6,320,029 B1 | 11/2001 | Miekka et al. |
| 6,461,610 B1 | 10/2002 | Kongsbak et al. |
| 6,586,573 B1 | 7/2003 | Besman et al. |
| 6,586,574 B1 | 7/2003 | Hansen |
| 6,599,724 B1 | 7/2003 | Mikaelsson et al. |
| 6,750,053 B1 | 6/2004 | Widrig Opalsky et al. |
| 6,806,063 B2 | 10/2004 | Pedersen et al. |
| 6,825,323 B2 | 11/2004 | Hess |
| 6,833,352 B2 | 12/2004 | Johannessen et al. |
| 6,858,587 B2 | 2/2005 | Sorensen et al. |
| 6,903,069 B2 | 6/2005 | Pingel et al. |
| 6,908,610 B1 | 6/2005 | Sato |
| 7,015,194 B2 | 3/2006 | Kjalke |
| 7,078,479 B2 | 7/2006 | Rojkjaer |
| 7,125,846 B2 | 10/2006 | Rojkjaer |
| 7,173,000 B2 | 2/2007 | Ruf et al. |
| 2001/0031721 A1 | 10/2001 | Webb et al. |
| 2002/0110552 A1 | 8/2002 | Romisch et al. |
| 2002/0115590 A1 | 8/2002 | Johannessen et al. |
| 2003/0109446 A1 | 6/2003 | Rojkjaer |
| 2004/0009918 A1 | 1/2004 | Nedergaard et al. |
| 2004/0037893 A1 | 2/2004 | Hansen et al. |
| 2004/0043933 A1 | 3/2004 | Hansen et al. |
| 2005/0266006 A1 | 12/2005 | Rojkjaer |
| 2006/0009376 A1 | 1/2006 | Eibl |
| 2006/0013812 A1 | 1/2006 | Rojkjaer |
| 2006/0063714 A1 | 3/2006 | Jensen et al. |
| 2006/0160720 A1 | 7/2006 | Jensen et al. |
| 2007/0049523 A1 | 3/2007 | Hansen et al. |
| 2009/0075895 A1 | 3/2009 | Nedergaard et al. |
| 2010/0136622 A1 | 6/2010 | Krarup et al. |

FOREIGN PATENT DOCUMENTS

| | | |
|---|---|---|
| AU | 2003/289742 | 7/2004 |
| CA | 2304396 | 4/1999 |
| CA | 2315309 | 2/2001 |
| DE | 19853033 | 5/2000 |
| EP | 052874 | 6/1982 |
| EP | 62-195335 | 8/1987 |
| EP | 430200 | 6/1991 |
| EP | 547932 | 6/1993 |
| EP | 765669 | 4/1997 |
| EP | 770625 | 5/1997 |
| EP | 952215 | 10/1999 |
| EP | 1232753 | 8/2002 |
| EP | 872487 | 10/2006 |
| JP | 225160 | 6/1987 |
| JP | 3-155797 | 7/1991 |

(Continued)

OTHER PUBLICATIONS

Klausen, N.K., et al., J Chromatogr., vol. 718, pp. 195-202 (1995).
Tokokiyo, K., et al., Vox Sang, vol. 84, pp. 54-64 (2003).
Krarup, J.C., et al., Abstr Pap Am Chem Soc, vol. 225 (1-2), pp. BIO333 (2003).
International Search Report of Jul. 22, 2004.
Bach, R. et al., "Immunoaffinity Purification of Bovine Factor VII", Blood, 1984, vol. 63, No. 2, pp. 393-398.
Bajaj, S.P. et al., "Isolation and Characterization of Human Factor VII", The Journal of Biological Chemistry, 1981, vol. 256, No. 1, pp. 253-259.
Broze, G.J. et al., "Purification and Properties of Human Coagulation Factor VII", The Journal of Biological Chemistry, 1980, vol. 255, No. 4, pp. 1242-1247.
Dike, G.W.R. et al., "A Factor VII Concentrate for Therapeutic Use", British Journal of Haematology, 1980, vol. 45, pp. 107-118.

(Continued)

*Primary Examiner* — Tekchand Saidha
(74) *Attorney, Agent, or Firm* — Rosemarie R. Wilk-Orescan

(57) ABSTRACT

The present invention relates to a process for the purification of a protease.

12 Claims, 1 Drawing Sheet

FOREIGN PATENT DOCUMENTS

| | | |
|---|---|---|
| JP | 6-504678 | 6/1994 |
| JP | 8-509745 | 10/1996 |
| JP | 11-500408 | 1/1999 |
| JP | 2000-302689 | 10/2000 |
| JP | 2000/513720 | 10/2000 |
| NZ | 336548 | 9/2001 |
| WO | WO 88/00210 | 1/1988 |
| WO | WO 91/10439 | 7/1991 |
| WO | WO 92/15686 | 9/1992 |
| WO | WO 93/00807 | 1/1993 |
| WO | WO 94/05692 | 3/1994 |
| WO | WO 94/22905 | 10/1994 |
| WO | WO 94/26286 | 11/1994 |
| WO | WO 94/27631 | 12/1994 |
| WO | WO 95/28954 | 11/1995 |
| WO | WO 96/12800 | 5/1996 |
| WO | WO 97/14430 | 4/1997 |
| WO | WO 97/19687 | 6/1997 |
| WO | WO 97/26909 | 7/1997 |
| WO | WO 97/47651 | 12/1997 |
| WO | WO 98/12225 | 3/1998 |
| WO | WO 98/22619 | 5/1998 |
| WO | WO 98/48822 | 11/1998 |
| WO | WO 99/02160 | 1/1999 |
| WO | WO 99/49880 | 10/1999 |
| WO | WO 99/66031 | 12/1999 |
| WO | WO 00/20835 | 4/2000 |
| WO | WO 00/48635 | 8/2000 |
| WO | WO 00/72873 | 12/2000 |
| WO | WO 01/03726 | 1/2001 |
| WO | WO 01/12653 | 2/2001 |
| WO | WO 01/17542 | 3/2001 |
| WO | WO 01/17567 | 3/2001 |
| WO | WO 01/17569 | 3/2001 |
| WO | WO 01/58935 | 8/2001 |
| WO | WO 01/82943 | 11/2001 |
| WO | WO 01/83725 | 11/2001 |
| WO | WO 01/85198 | 11/2001 |
| WO | WO 01/85199 | 11/2001 |
| WO | WO 02/17957 | 3/2002 |
| WO | WO 02/22776 | 3/2002 |
| WO | WO 03/092731 | 5/2002 |
| WO | WO 03/002524 | 1/2003 |
| WO | WO 03/007868 | 1/2003 |
| WO | WO 03/055511 | 7/2003 |
| WO | WO 03/055512 | 7/2003 |
| WO | WO 04/000347 | 12/2003 |
| WO | WO 04/082708 | 9/2004 |
| WO | WO 04/110469 | 12/2004 |

OTHER PUBLICATIONS

Dombrose, F.A. et al., "Evidence for Multiple Molecular Forms of Autoprothrombin C (Factor $X_a$)", Thrombosis Research, 1973, vol. 3, pp. 737-743.

Husi, H. et al., "Separation of Human Vitamin K-dependent Coagulation Proteins using Hydrophobic Interaction Chromatography", Journal of Chromatography B, 1999, vol. 736, pp. 77-88.

Jesty, J. et al., "Purification of Factor VII from Bovine Plasma", The Journal of Biological Chemistry, 1974, vol. 249, No. 2, pp. 509-515.

Liebman, H.A. et al., "Immunoaffinity Purification of Factor IX (Christmas factor) by Using Conformation-Specific Antibodies Directed Against the Factor Ix-Metal Complex", Proc. Natl. Acad. Sci. USA, 1985, vol. 82, pp. 3879-3883.

Nemerson, Y. et al., "Activation of a Proteolytic System by a Membrane Lipoprotein : Mechanism of Action of Tissue Factor ", Proc. Natl. Acad. Sci. USA, 1973, vol. 70, No. 2, pp. 310-314.

O'Brien, D.P. et al., "Purification and Characterization of Factor VII 304-Gln: A Variant Molecule With Reduced Activity Isolated From a Clinically Unaffected Male", Blood, 1991, vol. 78, No. 1, pp. 132-140.

Rao, L.V.M. et al., "Purification of Human Factor VII Utilizing O-(Diethylaminoethyl)- Sephadex and Sulfopropyl-Sephadex Chromatography", Analytical Biochemistry, 1984, vol. 136, pp. 357-361.

Ruiz, S.M. et al., "Expression and Purification of Recombinant Rabbit Factor VII", Thrombosis Research, 2000, vol. 98, pp. 203-211.

Yan, S.B., "Review of Conformation-Specific Affinity Purification Methods for Plasma Vitamin K-Dependent Proteins", Journal of Molecular Recognition, 1996, vol. 9, pp. 211-218 (1996).

Brozovic et al., 1971, "Stability of Prothrombin and Factor VII in Freeze-Dried Plasma," Journal of Clinical Pathology 24:690-693.

Cleland et al., 1993, "The Development of Stable Protein Formulations: A Close Look at Protein Aggregation, Deamidation, and Oxidation," Critial Reviews in Therapeutic Drug Carrier Systems 10(4):307-377.

Cooper, 1983, "Biochemistry of Sulfur-Containing Amino Acids," Annual Review of Biochemistry 52:187-222.

Krylov, Chief Editor, 2001, Enziklopedia Lekarstv. M., RLS-2001, 468: Encyclopedia of Drugs, p. 468.

English Translation of Krylov, Chief Editor, 2001, Enziklopedia Lekarstv. M., (Encyclopaedia of Medicines/Drugs) RLS-2001, 468; Encyclopedia of Drugs, pp. 468.

Manning et al., 1989, "Stability of Protein Pharmaceuticals," Pharmaceutical Research 6(11):903-918.

Novo Nordisk, 2000, "Koagulationsfaktor VIIA," Lægemiddel Kataloget pp. 893-894 and English Translation.

Novo Nordisk A/S, 1999, Novoseven(R) Coagulation Factor VIIA (Recombinant) Package Insert.

Novo Nordisk, 1999, "Novoseven Coagulation Factor VIIA (Recombinant)," FDA Article Online pp. 1-24.

PCT/DK2004/000181 International Search Report, dated Feb. 9, 2005.

PCT/DK03/00419 International Search Report, dated Oct. 20, 2003.

Porter et al., 1984, "Growth Inhibition by Methionine Analog Inhibitors of S-Adenosylmethionine Biosynthesis in the Absence of Polyamine Depletion," Biochemical and Biophysical Research Communications 122(1):350-357.

Wang, 2000, "Lyophilization and Development of Solid Protein Pharmaceuticals," International Journal of Pharmaceutics 203: 1-60.

Wang et al., 1988, "Parenteral Formulations of Proteins and Peptides: Stability and Stabilizers," Journal of Parenteral Science & Technology 42(10):4-26.

Wang et al., 1988, "Parenteral Drug Association Objectives," Journal of Parenteral Science & Technology 42:2S.

Wells, 1990, "Additivity of Mutational Effects in Proteins," Biochemistry 29(37):8509-8517.

JP 3-155797 English Abstract, Mar. 7, 1991.

JP 8-509745 English Language Machine Translation, published Oct. 15, 1996.

JP 6-504678 English Abstract, Mar. 9, 2010.

JP 62-195335 English Abstract, Mar. 9, 2010.

JP 2000-513720 English Language Machine Translation, published Oct. 17, 2000 (Novo Nordisk A/S).

JP 11-500408 English Language Machine Translation, published Jan. 12, 1999 (ZymoGenetics and Novo Nordisk A/S).

Non-final Office Action mailed Feb. 7, 2006 in U.S. Appl. No. 10/602,838 filed Jun. 24, 2003 by Hansen et al.

Final Office Action mailed Oct. 12, 2006 in U.S. Appl. No. 10/602,838 filed Jun. 24, 2003 by Hansen et al.

Advisory Action mailed Mar. 14, 2007 in U.S. Appl. No. 10/602,838 filed Jun. 24, 2003 by Hansen et al.

Non-Final Office Action mailed May 31, 2007 in U.S. Appl. No. 10/602,838 filed Jun. 24, 2003 by Hansen et al.

Final Office Action mailed Feb. 7, 2008 in U.S. Appl. No. 10/602,838 filed Jun. 24, 2003 by Hansen et al.

Advisory Action mailed Sep. 3, 2008 in U.S. Appl. No. 10/602,838 filed Jun. 24, 2003 by Hansen et al.

Non-Final Office Action mailed Feb. 6, 2009 in U.S. Appl. No. 10/602,838 filed Jun. 24, 2003 by Hansen et al.

Final Office Action mailed Jul. 31, 2009 in U.S. Appl. No. 10/602,838 filed Jun. 24, 2003 by Hansen et al.

Notice of Allowance mailed Dec. 8, 2009 in U.S. Appl. No. 10/602,838 filed Jun. 24, 2003 by Hansen et al.

Notice of Allowance mailed Mar. 29, 2010 in U.S. Appl. No. 10/602,838 filed Jun. 24, 2003 by Hansen et al.

Notice of Allowance mailed Jun. 22, 2010 in U.S. Appl. No. 10/602,838 filed Jun. 24, 2003 by Hansen et al.

Non-Final Office Action mailed Apr. 18, 2007 in U.S. Appl. No. 11/304,429 filed Dec. 15, 2005 by Hansen et al.

Non-Final Office Action mailed Nov. 20, 2007 in U.S. Appl. No. 11/304,429 filed Dec. 15, 2005 by Hansen et al.
Notice of Abandonment mailed Jun. 10, 2008 in U.S. Appl. No. 11/304,429 filed Dec. 15, 2005 by Hansen et al.
Non-Final Office Action mailed Jul. 29, 2009 in U.S. Appl. No. 12/154,088 filed May 20, 2008 by Hansen et al.
Notice of Allowance mailed Feb. 1, 2010 in U.S. Appl. No. 12/154,088 filed May 20, 2008 by Hansen et al.
Notice of Allowance mailed Apr. 14, 2010 in U.S. Appl. No. 12/154,088 filed May 20, 2008 by Hansen et al.
Notice of Allowance mailed Jul. 30, 2010 in U.S. Appl. No. 12/154,088 filed May 20, 2008 by Hansen et al.
Notice of Abandonment mailed Apr. 17, 2007 in U.S. Appl. No. 11/304,427 filed Dec. 15, 2005 by Jensen et al. And Decision of Petition to Reinstate Granted.
Non-Final Office Action mailed Sep. 11, 2007 in U.S. Appl. No. 11/304,427 filed Dec. 15, 2005 by Jensen et al.
Final Office Action mailed May 2, 2008 in U.S. Appl. No. 11/304,427 filed Dec. 15, 2005 by Jensen et al.
Advisory Action mailed Oct. 23, 2008 in U.S. Appl. No. 11/304,427 filed Dec. 15, 2005 by Jensen et al.
Non-Final Office Action mailed Feb. 6, 2009 in U.S. Appl. No. 11/304,427 filed Dec. 15, 2005 by Jensen et al.
Notice of Allowance mailed Dec. 15, 2009 in U.S. Appl. No. 11/304,427 filed Dec. 15, 2005 by Jensen et al.
Notice of Allowance mailed Apr. 8, 2010 in U.S. Appl. No. 11/304,427 filed Dec. 15, 2005 by Jensen et al.
Non-Final Office Action mailed Jul. 2, 2010 in U.S. Appl. No. 12/536,872 filed Aug. 6, 2009 by Jensen et al.
Non-Final Office Action mailed Sep. 19, 2008 in U.S. Appl. No. 11/450,783 filed Jun. 9, 2006 by Hansen et al.
Notice of Abandonment mailed Apr. 7, 2009 in U.S. Appl. No. 11/450,783 filed Jun. 9, 2006 by Hansen et al.
Non-Final Office Action mailed Jul. 7, 2010 in U.S. Appl. No. 12/407,266 filed Mar. 19, 2009 by Hansen et al.
Notice of Abandonment mailed Aug. 2, 2006 in U.S. Appl. No. 10/602,340 filed Jun. 23, 2003 by Hansen et al.
Non-Final Office Action mailed Apr. 8, 2008 in U.S. Appl. No. 11/473,387 filed Jun. 21, 2006 by Hansen et al.
Non-Final Office Action mailed Jan. 29, 2009 in U.S. Appl. No. 11/473,387 filed Jun. 21, 2006 by Hansen et al.
Final Office Action mailed Dec. 30, 2009 in U.S. Appl. No. 11/473,387 filed Jun. 21, 2006 by Hansen et al.
Notice of Abandonment mailed Jul. 14, 2010 in U.S. Appl. No. 11/473,387 filed Jun. 21, 2006 by Hansen et al.
Non-Final Office Action mailed Mar. 27, 2006 in U.S. Appl. No. 10/609,780 filed Jun. 30, 2003 by Jensen et al.
Notice of Abandonment mailed Oct. 27, 2006 in U.S. Appl. No. 10/609,780 filed Jun. 30, 2003 by Jensen et al.
Non-Final Office Action mailed Apr. 6, 2009 in U.S. Appl. No. 11/526,503 filed Sep. 25, 2006 by Jensen et al.
Non-Final Office Action mailed Jan. 4, 2010 in U.S. Appl. No. 11/526,503 filed Sep. 25, 2006 by Jensen et al.
Non-Final Office Action mailed Jun. 14, 2006 in U.S. Appl. No. 10/427,395 filed May 1, 2003 by Nedergaard et al.
Final Office Action mailed Mar. 19, 2007 in U.S. Appl. No. 10/427,395 filed May 1, 2003 by Nedergaard et al.
Advisory Action mailed Aug. 3, 2007 in U.S. Appl. No. 10/427,395 filed May 1, 2003 by Nedergaard et al.
Non-Final Office Action mailed May. 30, 2008 in U.S. Appl. No. 10/427,395 filed May 1, 2003 by Nedergaard et al.
Notice of Abandonment mailed Jan. 5, 2009 in U.S. Appl. No. 10/427,395 filed May 1, 2003 by Nedergaard et al.
Non-Final Office Action mailed Nov. 21, 2007 in U.S. Appl. No. 11/229,427 filed Sep. 15, 2005 by Jensen et al.
Non-Final Office Action mailed Jun. 25, 2008 in U.S. Appl. No. 11/229,427 filed Sep. 15, 2005 by Jensen et al.
Final Office Action mailed Jan. 27, 2009 in U.S. Appl. No. 11/229,427 filed Sep. 15, 2005 by Jensen et al.
Advisory Action mailed Apr. 8, 2009 in U.S. Appl. No. 11/229,427 filed Sep. 15, 2005 by Jensen et al.
Notice of Allowance mailed Jun. 12, 2009 in U.S. Appl. No. 11/229,427 filed Sep. 15, 2005 by Jensen et al.
Notice of Abandonment mailed Nov. 19, 2009 in U.S. Appl. No. 11/229,427 filed Sep. 15, 2005 by Jensen et al.
Blajchman, 2001, "Novel platelet products, substitutes and alternatives," Transfusion Clinique et Biologique 8(3):267-271.
PCT/DK2004/000359 International Search Report dated Oct. 1, 2004.
Sichler et al., 2002, "Crystal Structures of Uninhibited Factor VIIa Link its Cofactor and Substrate-Assisted Activation to Specific Interactions," J. Molecular Biology 322(3):591-603.
DE 19853033 English Abstract May 25, 2000.
JP 2000-302689 Machine Translation, Oct. 31, 2000.
Non-Final Office Action mailed Jun. 8, 2010 in U.S. Appl. No. 12/617,471 filed Nov. 12, 2009 by Jensen et al.
Final Office Action mailed Aug. 26, 2010 in U.S. Appl. No. 11/526,503 filed Sep. 25, 2006 by Jensen et al.
Notice of Allowance mailed Aug. 11, 2009 in U.S. Appl. No. 11/353,335 filed Feb. 14, 2006 by Jensen et al.
Non-Final Office Action mailed Jan. 13, 2009 in U.S. Appl. No. 11/353,335 filed Feb. 14, 2006 by Jensen et al.
Non-Final Office Action mailed Jul. 11, 2008 in U.S. Appl. No. 11/353,335 filed Feb. 14, 2006 by Jensen et al.
Non-Final Office Action mailed Aug. 27, 2010 in U.S. Appl. No. 11/284,709 filed Nov. 22, 2005 by Jensen et al.
Final Office Action mailed Feb. 19, 2010 in U.S. Appl. No. 11/284,709 filed Nov. 22, 2005 by Jensen et al.
Non-Final Office Action mailed Jun. 4, 2009 in U.S. Appl. No. 11/284,709 filed Nov. 22, 2005 by Jensen et al.
Non-Final Office Action mailed Sep. 25, 2008 in U.S. Appl. No. 11/284,709 filed Nov. 22, 2005 by Jensen et al.
Non-Final Office Action mailed Aug. 6, 2007 in U.S. Appl. No. 11/284,709 filed Nov. 22, 2005 by Jensen et al.

SEQUENCE LISTING

```
<160> NUMBER OF SEQ ID NOS: 1

<210> SEQ ID NO 1
<211> LENGTH: 406
<212> TYPE: PRT
<213> ORGANISM: Human
<220> FEATURE:
<221> NAME/KEY: MISC_FEATURE
<222> LOCATION: (1)..(406)
<223> OTHER INFORMATION: Xaa=gamma carboxyglutamic acid

<400> SEQUENCE: 1

Ala Asn Ala Phe Leu Xaa Xaa Leu Arg Pro Gly Ser Leu Xaa Arg Xaa
1               5                   10                  15

Cys Lys Xaa Xaa Gln Cys Ser Phe Xaa Xaa Ala Arg Xaa Ile Phe Lys
            20                  25                  30

Asp Ala Xaa Arg Thr Lys Leu Phe Trp Ile Ser Tyr Ser Asp Gly Asp
        35                  40                  45

Gln Cys Ala Ser Ser Pro Cys Gln Asn Gly Gly Ser Cys Lys Asp Gln
    50                  55                  60

Leu Gln Ser Tyr Ile Cys Phe Cys Leu Pro Ala Phe Glu Gly Arg Asn
65                  70                  75                  80

Cys Glu Thr His Lys Asp Asp Gln Leu Ile Cys Val Asn Glu Asn Gly
                85                  90                  95

Gly Cys Glu Gln Tyr Cys Ser Asp His Thr Gly Thr Lys Arg Ser Cys
            100                 105                 110

Arg Cys His Glu Gly Tyr Ser Leu Leu Ala Asp Gly Val Ser Cys Thr
        115                 120                 125

Pro Thr Val Glu Tyr Pro Cys Gly Lys Ile Pro Ile Leu Glu Lys Arg
    130                 135                 140
```

```
Asn Ala Ser Lys Pro Gln Gly Arg Ile Val Gly Gly Lys Val Cys Pro
145                 150                 155                 160

Lys Gly Glu Cys Pro Trp Gln Val Leu Leu Leu Val Asn Gly Ala Gln
            165                 170                 175

Leu Cys Gly Gly Thr Leu Ile Asn Thr Ile Trp Val Val Ser Ala Ala
            180                 185                 190

His Cys Phe Asp Lys Ile Lys Asn Trp Arg Asn Leu Ile Ala Val Leu
        195                 200                 205

Gly Glu His Asp Leu Ser Glu His Asp Gly Asp Glu Gln Ser Arg Arg
        210                 215                 220

Val Ala Gln Val Ile Ile Pro Ser Thr Tyr Val Pro Gly Thr Thr Asn
225                 230                 235                 240

His Asp Ile Ala Leu Leu Arg Leu His Gln Pro Val Val Leu Thr Asp
            245                 250                 255

His Val Val Pro Leu Cys Leu Pro Glu Arg Thr Phe Ser Glu Arg Thr
            260                 265                 270

Leu Ala Phe Val Arg Phe Ser Leu Val Ser Gly Trp Gly Gln Leu Leu
            275                 280                 285

Asp Arg Gly Ala Thr Ala Leu Glu Leu Met Val Leu Asn Val Pro Arg
            290                 295                 300

Leu Met Thr Gln Asp Cys Leu Gln Gln Ser Arg Lys Val Gly Asp Ser
305                 310                 315                 320

Pro Asn Ile Thr Glu Tyr Met Phe Cys Ala Gly Tyr Ser Asp Gly Ser
            325                 330                 335

Lys Asp Ser Cys Lys Gly Asp Ser Gly Gly Pro His Ala Thr His Tyr
            340                 345                 350

Arg Gly Thr Trp Tyr Leu Thr Gly Ile Val Ser Trp Gly Gln Gly Cys
            355                 360                 365

Ala Thr Val Gly His Phe Gly Val Tyr Thr Arg Val Ser Gln Tyr Ile
        370                 375                 380

Glu Trp Leu Gln Lys Leu Met Arg Ser Glu Pro Arg Pro Gly Val Leu
385                 390                 395                 400

Leu Arg Ala Pro Phe Pro
            405
```

US 7,897,734 B2

METHOD FOR THE PRODUCTION OF PROTEINS

CROSS-REFERENCE TO RELATED APPLICATIONS

This application is a Continuation of International Patent Application PCT/DK2004/000183 (published as WO 2004/083421), filed on Mar. 18, 2004, which claimed priority of Danish Patent Application PA 2003 00413, filed Mar. 18, 2003; this application further claims priority under 35 U.S.C §119of U.S Provisional Application 60/457,809, filed Mar. 26, 2003.

FIELD OF THE INVENTION

The present invention relates to methods for the production, purification and formulation of protease proteins.

BACKGROUND OF THE INVENTION

Many proteins involved in the clotting cascade, including, e.g., Factor VII, Factor VIII, Factor IX, Factor X, and Factor XIII, are proving to be useful therapeutic agents to treat a variety of pathological conditions. Generally, the blood components which participate in what has been referred to as the coagulation "cascade" are proenzymes or zymogens, enzymatically inactive proteins which are converted to proteolytic enzymes by the action of an activator, itself an activated clotting factor. Coagulation factors that have undergone such a conversion and generally referred to as "active factors," and are designated by the addition of a lower case "a" suffix (e.g., activated factor VII (FVIIa)).

Because of the many disadvantages of using human plasma as a source of pharmaceutical products, it is preferred to produce these proteins in recombinant systems. The clotting proteins, however, are subject to a variety of co- and post-translational modifications, including, e.g., asparagine-linked (N-linked) glycosylation; O-linked glycosylation; and γ-carboxylation of glu residues. For this reason, it is preferable to produce them in mammalian cells, which are able to modify the recombinant proteins appropriately.

In the production of clotting proteins from cultures of microorganisms or cell lines, the final production step is the recovery and optionally the concentration of the product of interest. Culture media in which the cells have been grown and which contain secreted proteins, and, in particular, cell lysates containing intracellular proteins of interest also contain, to a greater or lesser extent, other proteins produced by the cells, apart from other contaminants, such as media components, nucleic acids and the like. In order to obtain a purified protein product, it is therefore necessary to separate the protein of interest from other proteins and polypeptides and other impurities in the crude material containing the protein of interest.

U.S. Pat. No. 5,700,914 relates to a method for FVII purification, wherein zinc is present in at least in one of the purification steps.

During the traditional steps of cultivation, purification and in the traditional formulations the activated clotting proteins have a tendency to autodegrade due to the proteolytic function of the proteins. Thus, there is a need in the art for improved methods for cultivation, purification and formulation of activated clotting proteins to reduce the autodegradation during the production of clotting proteins, particularly recombinant human Factor VII or Factor VII-related polypeptides.

SUMMARY OF THE INVENTION

The present invention relates in a broad aspect to the purification of proteases. The process described herein may be applicable to the purification of any protease including coagulation factors FXII/FXIIa, FXI/FXIa, FX/FXa, FIX/FIXa, FVII/FVIIa, thrombin, and the anticoagulants protein C. Preferably the process is used for the purification of recombinant proteases produced under cell culture conditions. Preferably the process is used for the purification of serine proteases containing GLA (gamma-carboxyglutamic acid) residues, the vitamin K-dependent coagulation factors VIIa, IXa, Xa, activated protein C, and thrombin.

More preferably the serine proteases containing a domain with GLA (gamma-carboxyglutamate) residues is a Factor IX polypeptide, such as FIXa. Even more preferably the serine proteases containing a domain with GLA (gamma-carboxyglutamate) residues is a Factor VII polypeptide, such as FVIIa.

In a first aspect the present invention relates to a method for production of a purified GLA-residue containing serine protease, the method comprising:
  (i) culturing a host cell expressing the GLA-residue containing serine protease in a culture medium under conditions appropriate for expression of the GLA-residue containing serine protease;
  (ii) recovering all or part of the culture medium comprising the GLA-residue containing serine protease; and
  (iii) purifying the GLA-residue containing serine protease from the culture medium;
wherein the free calcium ion concentration under step (iii) is higher than 1.2 mM or lower than 0.10 mM; and/or
wherein the free ion concentration of a divalent metal cation other than a zinc ion and a calcium ion under step (iii) is higher than 0.025 mM; and/or
wherein the pH under step (iii) is lower than 7.5 or higher than 8.6.

In a second aspect the present invention relates to a method for production of a purified Factor VII polypeptide, the method comprising:
  (i) culturing a host cell expressing the Factor VII polypeptide in a culture medium under conditions appropriate for expression of the Factor VII polypeptide;
  (ii) recovering all or part of the culture medium comprising the Factor VII polypeptide; and
  (iii) purifying the Factor VII polypeptide from the culture medium;
wherein the free calcium ion concentration under step (iii) is higher than 1.2 mM or lower than 0.10 mM; and/or
wherein the free ion concentration of a divalent metal cation other than a zinc ion and a calcium ion under step (iii) is higher than 0.025 mM; and/or
wherein the pH under step (iii) is lower than 7.5 or higher than 8.6.

In a third aspect the present invention relates to a method for production of a purified GLA-residue containing serine protease, the method comprising:
  (i) culturing a host cell expressing the GLA-residue containing serine protease in a culture medium under conditions appropriate for expression of the GLA-residue containing serine protease;
  (ii) recovering all or part of the culture medium comprising the GLA-residue containing serine protease; and (iii) purifying the GLA-residue containing serine protease from the culture medium;
wherein the molar ratio of calcium ions and GLA-residue containing serine protease ($Ca^{2+}$:GLA-residue containing serine protease) under step (iii) is higher than 20 or lower than 0.50; and/or
wherein the free ion concentration of a divalent metal cation other than a zinc ion and a calcium ion under step (iii) is higher than 0.025 mM; and/or
wherein the pH under step (iii) is lower than 7.5 or higher than 8.6.

In a further aspect the present invention relates to a method for production of a purified Factor VII polypeptide, the method comprising:
 (i) culturing a host cell expressing the Factor VII polypeptide in a culture medium under conditions appropriate for expression of the Factor VII polypeptide;
 (ii) recovering all or part of the culture medium comprising the Factor VII polypeptide; and
 (iii) purifying the Factor VII polypeptide from the culture medium;
wherein the molar ratio of calcium ions and Factor VII polypeptide ($Ca^{2+}$:FVII polypeptide) under step (iii) is higher than 20 or lower than 0.50; and/or
wherein the free ion concentration of a divalent metal cation other than a zinc ion and a calcium ion under step (iii) is higher than 0.025 mM; and/or
 wherein the pH under step (iii) is lower than 7.5 or higher than 8.6.

In a further aspect the present invention relates to a method for the purification of a GLA-residue containing serine protease, the method comprising:
 (i) recovering all or part of a solution comprising the GLA-residue containing serine protease; and
 (ii) purifying the GLA-residue containing serine protease from the solution;
wherein the molar ratio of calcium ions and GLA-residue containing serine protease ($Ca^{2+}$:GLA-residue containing serine protease) under step (ii) is higher than 20 or lower than 0.50; and/or
wherein the free ion concentration of a divalent metal cation other than a zinc ion and a calcium ion under step (ii) is higher than 0.025 mM; and/or
wherein the pH under step (ii) is lower than 7.5 or higher than 8.6.

In a further aspect the present invention relates to a method for the purification of a Factor VII polypeptide, the method comprising:
 (i) recovering all or part of a solution comprising the Factor VII polypeptide; and
 (ii) purifying the Factor VII polypeptide from the solution;
wherein the molar ratio of calcium ions and Factor VII polypeptide ($Ca^{2+}$:FVII polypeptide) under step (ii) is higher than 20 or lower than 0.50; and/or
wherein the free ion concentration of a divalent metal cation other than a zinc ion and a calcium ion under step (ii) is higher than 0.025 mM; and/or
wherein the pH under step (ii) is lower than 7.5 or higher than 8.6.

In a further aspect the present invention relates to a method for the purification of a GLA-residue containing serine protease, the method comprising:
 (i) recovering all or part of a solution comprising the GLA-residue containing serine protease; and
 (ii) purifying the GLA-residue containing serine protease from the solution;
wherein the free calcium ion concentration under step (ii) is higher than 1.2 mM or lower than 0.10 mM; and/or
wherein the free ion concentration of a divalent metal cation other than a zinc ion and a calcium ion under step (ii) is higher than 0.025 mM; and/or
wherein the pH under step (ii) is lower than 7.5 or higher than 8.6.

In a further aspect the present invention relates to a method for the purification of a Factor VII polypeptide, the method comprising:
 (i) recovering all or part of a solution comprising the Factor VII polypeptide; and
 (ii) purifying the Factor VII polypeptide from the solution;
wherein the free calcium ion concentration under step (ii) is higher than 1.2 mM or lower than 0.10 mM; and/or
wherein the free ion concentration of a divalent metal cation other than a zinc ion and a calcium ion under step (ii) is higher than 0.025 mM; and/or
wherein the pH under step (ii) is lower than 7.5 or higher than 8.6.

In a further aspect the present invention relates to a process for the purification of a GLA-residue containing serine protease whereby a solution of a GLA-residue containing serine protease is subjected to a number of purification steps, wherein the free calcium ion concentration at least in one of the purification steps is higher than 1.2 mM or lower than 0.10 mM; and/or
wherein the free ion concentration of a divalent metal cation other than a zinc ion and a calcium ion at least in one of the purification steps is higher than 0.025 mM; and/or
wherein the pH at least in one of the purification steps is lower than 7.5 or higher than 8.6. is present.

In a further aspect the present invention relates to a process for the purification of a Factor VII polypeptide whereby a solution of a Factor VII polypeptide is subjected to a number of purification steps, wherein the free calcium ion concentration at least in one of the purification steps is higher than 1.2 mM or lower than 0.10 mM; and/or
wherein the free ion concentration of a divalent metal cation other than a zinc ion and a calcium ion at least in one of the purification steps is higher than 0.025 mM; and/or
wherein the pH at least in one of the purification steps is lower than 7.5 or higher than 8.6. is present.

In a further aspect the present invention relates to a process for the purification of a GLA-residue containing serine protease whereby a solution of a GLA-residue containing serine protease is subjected to a number of purification steps, wherein the molar ratio of calcium ions and GLA-residue containing serine protease ($Ca^{2+}$:GLA-residue containing serine protease) at least in one of the purification steps is higher than 20 or lower than 0.50; and/or
wherein the free ion concentration of a divalent metal cation other than a zinc ion and a calcium ion at least in one of the purification steps is higher than 0.025 mM; and/or
wherein the pH at least in one of the purification steps is lower than 7.5 or higher than 8.6. is present.

In a further aspect the present invention relates to a process for the purification of a Factor VII polypeptide whereby a solution of a Factor VII polypeptide is subjected to a number of purification steps, wherein the molar ratio of calcium ions and Factor VII polypeptide ($Ca^{2+}$:FVII polypeptide) at least in one of the purification steps is higher than 20 or lower than 0.50; and/or
wherein the free ion concentration of a divalent metal cation other than a zinc ion and a calcium ion at least in one of the purification steps is higher than 0.025 mM; and/or wherein the pH at least in one of the purification steps is lower than 7.5 or higher than 8.6. is present.

In a further aspect the present invention relates to a method for stabilizing a GLA-residue containing serine protease in a solution comprising the GLA-residue containing serine protease whereby the solution comprising the GLA-residue containing serine protease is subjected to the steps of, adding calcium to obtain a free calcium ion concentration higher than 1.2 mM or lower than 0.10 mM; and/or adding a divalent metal cation other than a zinc ion and a calcium ion to obtain a the free ion concentration of a divalent metal cation other than a zinc ion and a calcium ion higher than 0.025 mM; and/or adjusting the pH of the solution comprising a GLA-residue containing serine protease to a pH lower than 7.5 or higher than 8.6.

In a further aspect the present invention relates to a method for stabilizing a Factor VII polypeptide in a solution comprising the Factor VII polypeptide whereby the solution comprising the Factor VII polypeptide is subjected to the steps of, adding calcium to obtain a free calcium ion concentration higher than 1.2 mM or lower than 0.10 mM; and/or adding a divalent metal cation other than a zinc ion and a calcium ion to obtain a the free ion concentration of a divalent metal cation other than a zinc ion and a calcium ion higher than 0.025 mM; and/or adjusting the pH of the solution comprising a Factor VII polypeptide to a pH lower than 7.5 or higher than 8.6.

In a further aspect the present invention relates to a composition comprising (i) a GLA-residue containing serine protease (ii) a free calcium ions in a concentration higher than 1.2 mM or lower than 0.10 mM; and/or a free divalent metal cation other than zinc ions and calcium ions in a concentration higher than 0.025 mM; and/or wherein the pH of the composition has a pH lower than 7.5 or higher than 8.6.

In a further aspect the present invention relates to a composition comprising (i) a Factor VII polypeptide (ii) a free calcium ions in a concentration higher than 1.2 mM or lower than 0.10 mM; and/or a free divalent metal cation other than zinc ions and calcium ions in a concentration higher than 0.025 mM; and/or wherein the pH of the composition has a pH lower than 7.5 or higher than 8.6.

DETAILED DESCRIPTION OF THE INVENTION

Figure 1:
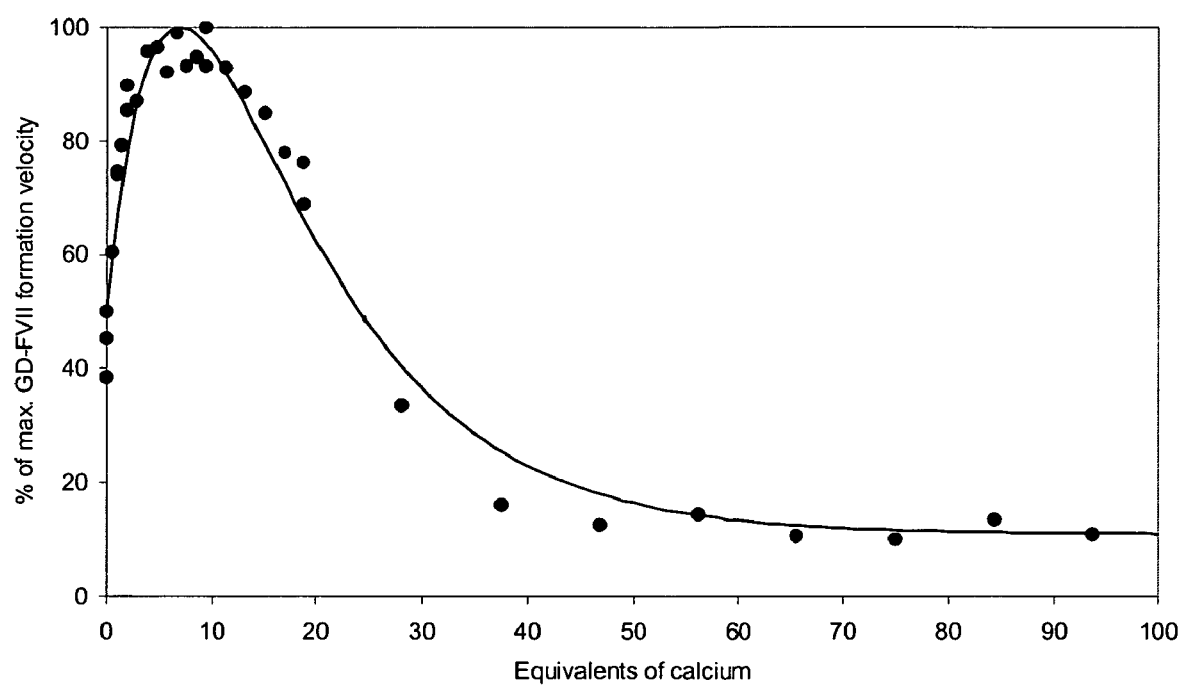
FIG. 1 is a graphic illustration showing the formation of FVIIa without a GLA domain (GD-FVIIa). The figure shows the velocity of GD-FVIIa formation versus FVIIa to $Ca^{2+}$ molar ratio (Equivalents of calcium =FVIIa:$Ca^{2+}$). Conditions were: 1.3 mg/ml FVIIa, 75 mM NaCl, 10 mM glycylglycine, pH 8.5.

In order to reduce autodegration of hyperactive FVII(a) analogues, e.g. variants of FVII polypeptides with proteolytic activity higher than wild type human FVIIa, the activity and liability is reduced processing a) in the presence of >25 micromolar of a divalent metal cation other than a zinc ion and a calcium ion, e.g. $Cu^{2+}$ during purification, and/or b) in the presence of >1.2 mM $Ca^{2+}$ during purification and/or c) in the presence of <0.1 mM $Ca^{2+}$ during purification and/or d) at pH lower 7.5 during purification and/or e) at pH higher than 8.6 during purification.

Autodegradation of hyperactive FVIIa analogues is severe at neutral pH (pH=7.5) and cause considerable reduction of yield throughout the purification process. Known solutions include the introduction of either highly toxic protease inhibitors into the purification process or expensive "tailored" inhibitors or scavenger peptides/proteins.

Stabilisation of culture supernatant, immunoaffinity capture and purification by anion exchange carried out at pH 6 have by the inventors of the present invention been shown to have an enormous advantage over the known FVII purification processes.

One aspect of the present invention related to a method for production of a purified Factor VII polypeptide, the method comprising:

(i) culturing a host cell expressing the Factor VII polypeptide in a culture medium under conditions appropriate for expression of the Factor VII polypeptide;

(ii) recovering all or part of the culture medium comprising the Factor VII polypeptide; and (iii) purifying the Factor VII polypeptide from the culture medium;

wherein the free calcium ion concentration under step (iii) is higher than 1.2 mM or lower than 0.10 mM; and/or wherein the free ion concentration of a divalent metal cation other than a zinc ion and a calcium ion under step (iii) is higher than 0.025 mM; and/or wherein the pH under step (iii) is lower than 7.5 or higher than 8.6.

In a second aspect the present invention relates to a method for production of a purified Factor VII polypeptide, the method comprising:

(i) culturing a host cell expressing the Factor VII polypeptide in a culture medium under conditions appropriate for expression of the Factor VII polypeptide;

(ii) recovering all or part of the culture medium comprising the Factor VII polypeptide; and (iii) purifying the Factor VII polypeptide from the culture medium;

wherein the molar ratio of calcium ions and Factor VII polypeptide ($Ca^{2+}$:FVII polypeptide) under step (iii) is higher than 20 or lower than 0.50; and/or wherein the free ion concentration of a divalent metal cation other than a zinc ion and a calcium ion under step (iii) is higher than 0.025 mM; and/or wherein the pH under step (iii) is lower than 7.5 or higher than 8.6.

In a third aspect the present invention relates to a method for the purification of a Factor VII polypeptide, the method comprising:

(i) recovering all or part of a solution comprising the Factor VII polypeptide; and (ii) purifying the Factor VII polypeptide from the solution;

wherein the molar ratio of calcium ions and Factor VII polypeptide ($Ca^{2+}$:FVII polypeptide) under step (ii) is higher than 20 or lower than 0.50; and/or wherein the free ion concentration of a divalent metal cation other than a zinc ion and a calcium ion under step (ii) is higher than 0.025 mM; and/or wherein the pH under step (ii) is lower than 7.5 or higher than 8.6.

In a further aspect the present invention relates to a method for the purification of a Factor VII polypeptide, the method comprising:
(i) recovering all or part of a solution comprising the Factor VII polypeptide; and
(ii) purifying the Factor VII polypeptide from the solution; wherein the free calcium ion concentration under step (ii) is higher than 1.2 mM or lower than 0.10 mM; and/or
wherein the free ion concentration of a divalent metal cation other than a zinc ion and a calcium ion under step (ii) is higher than 0.025 mM; and/or
wherein the pH under step (ii) is lower than 7.5 or higher than 8.6.

In a further aspect the present invention relates to a process for the purification of a Factor VII polypeptide whereby a solution of a Factor VII polypeptide is subjected to a number of purification steps, wherein the free calcium ion concentration at least in one of the purification steps is higher than 1.2 mM or lower than 0.10 mM; and/or
wherein the free ion concentration of a divalent metal cation other than a zinc ion and a calcium ion at least in one of the purification steps is higher than 0.025 mM; and/or
wherein the pH at least in one of the purification steps is lower than 7.5 or higher than 8.6. is present.

In a further aspect the present invention relates to a process for the purification of a Factor VII polypeptide whereby a solution of a Factor VII polypeptide is subjected to a number of purification steps, wherein the molar ratio of calcium ions and Factor VII polypeptide ($Ca^{2+}$:FVII polypeptide) at least in one of the purification steps is higher than 20 or lower than 0.50; and/or
wherein the free ion concentration of a divalent metal cation other than a zinc ion and a calcium ion at least in one of the purification steps is higher than 0.025 mM; and/or
wherein the pH at least in one of the purification steps is lower than 7.5 or higher than 8.6. is present.

In a further aspect the present invention relates to a method for stabilizing a Factor VII polypeptide in a solution comprising the Factor VII polypeptide whereby the solution comprising the Factor VII polypeptide is subjected to the steps of, adding calcium to obtain a free calcium ion concentration higher than 1.2 mM or lower than 0.10 mM; and/or
adding a divalent metal cation other than a zinc ion and a calcium ion to obtain a the free ion concentration of a divalent metal cation other than a zinc ion and a calcium ion higher than 0.025 mM; and/or
adjusting the pH of the solution comprising a Factor VII polypeptide to a pH lower than 7.5 or higher than 8.6.

In a further aspect the present invention relates to a method for production of a purified GLA-residue containing serine protease, the method comprising:
(i) culturing a host cell expressing said GLA-residue containing serine protease in a culture medium under conditions appropriate for expression of said GLA-residue containing serine protease;
(ii) recovering all or part of the culture medium comprising said GLA-residue containing serine protease; and
(iii) purifying said GLA-residue containing serine protease from the culture medium;
wherein the pH under step (iii) has a value between 4.5 and 6.9 or has a value between 8.6 and 10.

In a further aspect the present invention relates to a method for the purification of a GLA-residue containing serine protease whereby a solution of a GLA-residue containing serine protease is subjected to a number of purification steps, wherein the pH at least in one of the purification steps has a value between 4.5 and 6.9 or has a value between 8.6 and 10.

In a further aspect the present invention relates to a method for stabilizing a GLA-residue containing serine protease in a solution comprising the GLA-residue containing serine protease whereby said solution comprising the GLA-residue containing serine protease is subjected to the steps of, adding calcium to obtain a free calcium ion concentration higher than 1.2 mM or lower than 0.10 mM; and/or
adding a divalent metal cation other than a zinc ion and a calcium ion to obtain a the free ion concentration of a divalent metal cation other than a zinc ion and a calcium ion higher than 0.025 mM; and/or
adjusting the pH of the solution comprising a GLA-residue containing serine protease to a value between 4.5 and 6.9 or to a value between 8.6 and 10.

In a further aspect the present invention relates to a composition comprising a GLA-residue containing serine protease in a solution with a pH at a value between 4.5 and 6.9 or has a value between 8.6 and 10.

The term "GLA-residue containing serine protease" as used herein means a protein selected from the group consisting of Factors VII polypeptides, Factor IX polypeptides, Factor X and variants and derivatives thereof, protein C and variants and derivatives thereof, and prothrombin/thrombin and variants and derivatives thereof, wherein the protein contains one or more gamma-carboxyglutamic acid (GLA) amino acid residue. In one embodiment the GLA-residue containing serine protease is the active form of the protein, such as Factor VI la, Factor IXa, Factor Xa, activated protein C, and thrombin. In one embodiment the GLA-residue containing serine protease is human.

By "stabilizing" a GLA-residue containing serine protease, such as a Factor VII polypeptide or a Factor IX polypeptide in a composition comprising the serine protease is meant decreasing the degree of degradation, i.e. amount of degradation products per time unit, of the serine protease in the composition, e.g. proteolytic or chemical degradation. Preferably the degradation as measured in the GD-FVIIa formation velocity assay described herein is less than 60% of maximum GD-FVIIa formation, such as 50% of maximum GD-FVIIa formation, such as 40% of maximum GD-FVIIa formation, such as 30% of maximum GD-FVIIa formation, such as 20% of maximum GD-FVIIa formation, such as 10% of maximum GD-FVIIa formation.

It is to be understood that by "stabilizing" a GLA-residue containing serine protease in a composition is meant an increase in stability during any step in the process of recombinant protein production, the step being selected from the group consisting of harvest, capture, storage, handling, processing, purification, bulk preformulation, bulk formulation, ultra/diafiltration, ion exchange, anion exchange capture, size exclusion chromatography, hydrophobic interaction chromatography, percipitation and affinity purification.

The term "purified GLA-residue containing serine protease" as used herein, means a GLA-residue containing serine protease that has been separated from at least about 50 percent by weight of polynucleotides, lipids, carbohydrates and any other contaminating polypeptides or other contaminants that are found in the culture medium following expression in a eukaryotic host cells which would interfere with its therapeutic, diagnostic, prophylactic or research use. The GLA-residue containing serine protease can be purified to be substantially free of natural contaminants from the culture medium through the use of any of a variety of methodologies. Standard chromatographic separation technology for the purification of the GLA-residue containing serine protease may also be used in some of the purification steps.

The term "purified Factor VII polypeptide" as used herein, means a Factor VII polypeptide that has been separated from at least about 50 percent by weight of polynucleotides, lipids, carbohydrates and any other contaminating polypeptides or other contaminants that are found in the culture medium following expression in a eukaryotic host cells which would interfere with its therapeutic, diagnostic, prophylactic or research use. The Factor VII polypeptide can be purified to be substantially free of natural contaminants from the culture medium through the use of any of a variety of methodologies. Standard chromatographic separation technology for the purification of the Factor VII polypeptide may also be used in some of the purification steps.

By "purifying" a polypeptide from a composition comprising the polypeptide and one or more contaminants is meant increasing the degree of purity of the polypeptide in the composition by removing (completely or partially) at least one contaminant from the composition. A "purification step" may be part of an overall purification process resulting in a "homogeneous" composition, which is used herein to refer to a composition comprising at least about 70% by weight of the polypeptide of interest, based on total weight of the composition, preferably at least about 80% by weight.

The term "free calcium ion concentration" as used herein means the concentration of divalent positive calcium ions ($Ca^{2+}$) surrounded by water molecules. The term does not include calcium in solid form, ie. in a crystal structure or calcium bound in proteins, such as FVII.

The term "free ion concentration of a divalent metal cation other than a zinc ion and a calcium ion" as used herein means the concentration of a divalent positive ion surrounded by water molecules, which is not a calcium ion or a zinc ion. The term does not include a divalent positive ion in solid form, ie. in a crystal structure or ions bound in proteins.

In one embodiment of the invention, the purifications steps are chromatographic purification steps.

In one embodiment of the invention, at least one purification step is hydrophobic interaction chromatography.

In one embodiment of the invention, at least one purification step is size exclusion chromatography.

In one embodiment of the invention, at least one purification step is anion exchange chromatography.

In one embodiment of the invention, at least one purification step is ultrafiltration.

In one embodiment of the invention, at least one purification step is immunoaffinity purification.

In one embodiment of the invention, at least one purification step is diafiltration.

In one embodiment of the invention, the free calcium ion concentration under step (iii) is higher than 1.2 mM. In one embodiment of the invention, the free calcium ion concentration under step (iii) is higher than 1.3 mM, such as higher than 1.4 mM, such as higher than 1.5 mM, such as higher than 1.6 mM, such as higher than 1.7 mM, such as higher than 1.8 mM, such as higher than 1.9 mM, such as higher than 2.0 mM, such as higher than 2.1 mM, such as higher than 2.2 mM, such as higher than 2.3 mM, such as higher than 2.4 mM, such as higher than 2.5 mM, such as higher than 2.6 mM, such as higher than 3.0 mM, such as higher than 4.0 mM, such as higher than 5.0 mM, such as higher than 6.0 mM, such as higher than 7.0 mM, such as higher than 8.0 mM, such as higher than 9.0 mM, such as higher than 10.0 mM, such as higher than 20 mM, such as higher than 40.0 mM, such as higher than 60.0 mM, such as higher than 80.0 mM, such as higher than 0.1 M, such as higher than 1 M, such as a free calcium ion concentration, where the solution is saturated.

The term "free calcium ion concentration, where the solution is saturated" as used herein means the concentration of free calcium ions, when the dissolved free calcium ions exists in equilibrium with undissolved calcium ion in solid form.

In one embodiment of the invention, the free calcium ion concentration under step (iii) is lower than 0.10 mM. In one embodiment of the invention, the free calcium ion concentration under step (iii) is lower than 0.09, such as lower than 0.08, such as lower than 0.07, such as lower than 0.06, such as lower than 0.05, such as lower than 0.04, such as lower than 0.03, such as lower than 0.02, such as lower than 0.01, such as lower than 0.00.

In one embodiment of the invention, the free ion concentration of a divalent metal cation other than a zinc ion and a calcium ion under step (iii) is higher than 0.025 mM. In one embodiment of the invention, the divalent metal cation is selected from the list consisting of $Mg^{2+}$, $Cu^{2+}$, $Mn^{2+}$, $Co^{2+}$, $Fe^{2+}$, $Sm^{2+}$, $Ni^{2+}$, $Cd^{2+}$, $Hg^{2+}$, $Sm^{2+}$, and $Uo^{2+}$. In one embodiment of the invention, the divalent metal cation is selected from the list consisting of $Mg^{2+}$, $Cu^{2+}$, and $Mn^{2+}$. In one embodiment of the invention, the free ion concentration of a divalent metal cation other than a zinc ion and a calcium ion under step (iii) is higher than 0.025 mM, such as higher than 0.03 mM, such as higher than 0.035 mM, such as higher than 0.04 mM, such as higher than 0.045 mM, such as higher than 0.05 mM, such as higher than 0.055 mM, such as higher than 0.06 mM, such as higher than 0.1 mM, such as higher than 0.15 mM, such as higher than 0.2 mM, such as higher than 0.25 mM, such as higher than 0.3 mM, such as higher than 0.5 mM, such as higher than 1.0 mM.

In one embodiment of the invention, the GLA-residue containing serine protease is purified under step (iii) in the presence of a further divalent metal ion chelator.

In one embodiment of the invention, the Factor VII polypeptide is purified under step (iii) in the presence of a further divalent metal ion chelator.

The term "divalent metal ion chelator" as used herein means any agent or compound, that removes or binds divalent metal ions, such as calcium ions or zinc ions. The divalent metal ion chelator may be a polycarboxylic acid chelating agent, citrate, bathocuproine, bathophenanthroline, DTPA, ethylenediaminetetraacetic acid (EDTA), EGTA, penicillamine, TETA, TPEN, and derivatives thereof.

In one embodiment of the invention, the GLA-residue containing serine protease is purified under step (iii) at a pH lower than 7.5. In one embodiment of the invention, the pH is lower than 7.4, such as lower than 7.3, such as lower than 7.2, such as lower than 7.1, such as lower than 7.0, such as lower than 6.8, such as lower than 6.6, such as lower than 6.4, such as lower than 6.2, such as lower than 6.0, such as 5.5.

In one embodiment of the invention, the GLA-residue containing serine protease is purified under step (iii) at a pH higher than 8.6. In one embodiment of the invention, the pH is higher than 8.7, such as higher than 8.8, such as higher than 8.9, such as higher than 9.0, such as higher than 9.1, such as higher than 9.2, such as higher than 9.4, such as higher than 9.6, such as higher than 9.8, such as higher than 10.0, such as higher than 10.2, such as higher than 10.4, such as higher than 10.8, such as 11.0.

In one embodiment of the invention, the Factor VII polypeptide is purified under step (iii) at a pH lower than 7.5. In one embodiment of the invention, the pH is lower than 7.4, such as lower than 7.3, such as lower than 7.2, such as lower than 7.1, such as lower than 7.0, such as lower than 6.8, such as lower than 6.6, such as lower than 6.4, such as lower than 6.2, such as lower than 6.0, such as 5.5.

In one embodiment of the invention, the Factor VII polypeptide is purified under step (iii) at a pH higher than 8.6. In one embodiment of the invention, the pH is higher than 8.7, such as higher than 8.8, such as higher than 8.9, such as higher than 9.0, such as higher than 9.1, such as higher than 9.2, such as higher than 9.4, such as higher than 9.6, such as higher than 9.8, such as higher than 10.0, such as higher than 10.2, such as higher than 10.4, such as higher than 10.8, such as 11.0.

In one embodiment of the invention, the GLA-residue containing serine protease is purified at a pH between 4.5 and 6.9. In one embodiment of the invention, the Factor VII polypeptide is purified at a pH between 4.5 and 6.9. In one embodiment of the invention, the pH is between 4.7 and 6.8, such as between 4.9 and 6.7, such as between 5.1 and 6.6, such as between 5.3 and 6.5, such as between 5.5 and 6.4, such as between 5.7 and 6.3, such as between 5.8 and 6.2, such as between 5.9 and 6.1, such as about 6.0.

In one embodiment of the invention, the GLA-residue containing serine protease is purified at a pH between 8.6 and 10. In one embodiment of the invention, the Factor VII polypeptide is purified at a pH between 8.6 and 10. In one embodiment of the invention, the pH is between 8.7 and 9.9, such as between 8.8 and 9.8, such as between 8.9 and 9.7, such as between 9.0 and 9.6, such as between 9.1 and 9.5, such as between 8.7 and 9.7, such as between 8.7 and 9.6, such as between 8.8 and 9.5, such as between 8.9 and 9.4, such as between 9.0 and 9.2, such as about 9.2.

In one embodiment of the invention, the GLA-residue containing serine protease is purified in the presence of histidine. It is to be understood that histidine may serve to buffer the pH at a range of 5-7 or 8-10.

In one embodiment of the invention, the Factor VII polypeptide is purified in the presence of histidine. It is to be understood that histidine may serve to buffer the pH at a range of 5-7 or 8-10.

In one embodiment of the invention, the host cell is a eukaryotic host cell.

In one embodiment of the invention, the eukaryotic host cell is a mammalian cell. In one embodiment of the invention, the mammalian cell is selected from the group consisting of HEK cells, BHK cells, CHO cells, COS cells, and myeloma cells such as SP2-0.

In one embodiment of the invention, the Factor VII polypeptide is wild-type human factor VII.

In one embodiment of the invention, the Factor VII polypeptide has a proteolytic activity higher than wild type human FVIIa.

In one embodiment of the invention, the Factor VII polypeptide is a factor VII-related polypeptide selected from the group consisting of: L305V-FVII, L305V/M306D/D309S-FVII, L3051-FVII, L305T-FVII, F374P-FVII, V158T/M298Q-FVII, V158D/E296V/M298Q-FVII, K337A-FVII, M298Q-FVII, V158D/M298Q-FVII, L305V/K337A-FVII, V158D/E296V/M298Q/L305V-FVII, V158D/E296V/M298Q/K337A-FVII, V158D/E296V/M298Q/L305V/K337A-FVII, K157A-FVII, E296V-FVII, E296V/M298Q-FVII, V158D/E296V-FVII, V158D/M298K-FVII, and S336G-FVII, L305V/K337A-FVII, L305V/V158D-FVII, L305V/E296V-FVII, L305V/M298Q-FVII, L305V/V158T-FVII, L305V/K337A/V158T-FVII, L305V/K337A/M298Q-FVII, L305V/K337A/E296V-FVII, L305V/K337A/V158D-FVII, L305V/V158D/M298Q-FVII, L305V/V158D/E296V-FVII, L305V/V158T/M298Q-FVII, L305V/V158T/E296V-FVII, L305V/E296V/M298Q-FVII, L305V/V158D/E296V/M298Q-FVII, L305V/V158T/E296V/V298Q-FVII, L305V/V158T/K337A/M298Q-FVII, L305V/V158T/E296V/K337A-FVII, L305V/V158D/K337A/M298Q-FVII, L305V/V158D/E296V/K337A-FVII, L305V/V158T/E296V/M298Q/K337A-FVII, L305V/V158T/E296V/M298Q/K337A-FVII, S314E/K316H-FVII, S314E/K316Q-FVII, S314E/L305V-FVII, S314E/K337A-FVII, S314E/V158D-FVII, S314E/E296V-FVII, S314E/M298Q-FVII, S314E/V158T-FVII, K316H/L305V-FVII, K316H/K337A-FVII, K316H/V158D-FVII, K316H/E296V-FVII, K316H/M298Q-FVII, K316H/V158T-FVII, K316Q/L305V-FVII, K316Q/K337A-FVII, K316Q/V158D-FVII, K316Q/E296V-FVII, K316Q/M298Q-FVII, K316Q/V158T-FVII, S314E/L305V/K337A-FVII, S314E/L305V/V158D-FVII, S314E/L305V/E296V-FVII, S314E/L305V/M298Q-FVII, S314E/L305V/V158T-FVII, S314E/L305V/K337A/V158T-FVII, S314E/L305V/K337A/M298Q-FVII, S314E/L305V/K337A/E296V-FVII, S314E/L305V/K337A/V158D-FVII, S314E/L305V/V158D/M298Q-FVII, S314E/L305V/V158D/E296V-FVII, S314E/L305V/V158T/M298Q-FVII, S314E/L305V/V158T/E296V-FVII, S314E/L305V/E296V/M298Q-FVII, S314E/L305V/V158D/E296V/M298Q-FVII, S314E/L305V/V158T/E296V/M298Q-FVII, S314E/L305V/V158T/K337A/M298Q-FVII, S314E/L305V/V158T/E296V/K337A-FVII, S314E/L305V/V158D/K337A/M298Q-FVII, S314E/L305V/V158D/E296V/K337A-FVII, S314E/L305V/V158D/E296V/M298Q/K337A-FVII, S314E/L305V/V158T/E296V/M298Q/K337A-FVII, K316H/L305V/K337A-FVII, K316H/L305V/V158D-FVII, K316H/L305V/E296V-FVII, K316H/L305V/M298Q-FVII, K316H/L305V/V158T-FVII, K316H/L305V/K337A/V158T-FVII, K316H/L305V/K337A/M298Q-FVII, K316H/L305V/K337A/E296V-FVII, K316H/L305V/K337A/V158D-FVII, K316H/L305V/V158D/M298Q-FVII, K316H/L305V/V158D/E296V-FVII, K316H/L305V/V158T/M298Q-FVII, K316H/L305V/V158T/E296V-FVII, K316H/L305V/E296V/M298Q-FVII, K316H/L305V/V158D/E296V/M298Q-FVII, K316H/L305V/V158T/E296V/M298Q-FVII, K316H/L305V/V158T/K337A/M298Q-FVII, K316H/L305V/V158T/E296V/K337A-FVII, K316H/L305V/V158D/K337A/M298Q-FVII, K316H/L305V/V158D/E296V/K337A-FVII, K316H/L305V/V158D/E296V/M298Q/K337A-FVII, K316H/L305V/V158T/E296V/M298Q/K337A-FVII, K316Q/L305V/K337A-FVII, K316Q/L305V/V158D-FVII, K316Q/L305V/E296V-FVII, K316Q/L305V/M298Q-FVII, K316Q/L305V/V158T-FVII, K316Q/L305V/K337A/V158T-FVII, K316Q/L305V/K337A/M298Q-FVII, K316Q/L305V/K337A/E296V-FVII, K316Q/L305V/K337A/V158D-FVII, K316Q/L305V/V158D/M298Q-FVII, K316Q/L305V/V158D/E296V-FVII, K316Q/L305V/V158T/M298Q-FVII, K316Q/L305V/V158T/E296V-FVII, K316Q/L305V/E296V/M298Q-FVII, K316Q/L305V/V158D/E296V/M298Q-FVII, K316Q/L305V/V158T/E296V/M298Q-FVII, K316Q/L305V/V158T/K337A/M298Q-FVII, K316Q/L305V/V158T/E296V/K337A-FVII, K316Q/L305V/V158D/K337A/M298Q-FVII, K316Q/L305V/V158D/E296V/K337A-FVII, K316Q/L305V/V158D/E296V/M298Q/K337A-FVII, K316Q/L305V/V158T/E296V/M298Q/K337A-FVII, F374Y/K337A-FVII, F374Y/V158D-FVII, F374Y/E296V-FVII, F374Y/M298Q-FVII, F374Y/V158T-FVII, F374Y/S314E-FVII, F374Y/L305V-FVII, F374Y/L305V/K337A-FVII, F374Y/L305V/V1158D-FVII, F374Y/L305V/E296V-FVII, F374Y/L305V/M298Q-FVII, F374Y/L305V/V158T-FVII, F374Y/L305V/S314E-FVII, F374Y/K337A/S314E-FVII, F374Y/K337A/V158T-FVII, F374Y/K337A/M298Q-FVII, F374Y/K337A/E296V-FVII, F374Y/K337A/V158D-FVII, F374Y/V158D/S314E-FVII, F374Y/V158D/M298Q-FVII, F374Y/V158D/E296V-FVII, F374Y/V158T/S314E-FVII, F374Y/V158T/M298Q-FVII, F374Y/V158T/E296V-FVII, F374Y/E296V/S314E-FVII, F374Y/S314E/M298Q-FVII, F374Y/E296V/M298Q-FVII, F374Y/L305V/K337A/V158D-FVII, F374Y/L305V/K337A/E296V-FVII, F374Y/L305V/K337A/M298Q-FVII, F374Y/L305V/K337A/V158T-FVII, F374Y/L305V/K337A/S314E-FVII, F374Y/L305V/V158D/E296V-FVII, F374Y/L305V/V158D/M298Q-FVII, F374Y/L305V/V158D/S314E-FVII, F374Y/L305V/E296V/M298Q-FVII, F374Y/L305V/E296V/V158T-FVII, F374Y/L305V/E296V/S314E-FVII, F374Y/L305V/M298Q/V158T-FVII, F374Y/L305V/M298Q/S314E-FVII, F374Y/L305V/V158T/S314E-FVII, F374Y/K337A/S314E/V158T-FVII, F374Y/K337A/S314E/M298Q-FVII, F374Y/K337A/S314E/E296V-FVII, F374Y/K337A/S314E/V158D-FVII, F374Y/K337A/V158T/M298Q-FVII, F374Y/K337A/V158T/E296V-FVII, F374Y/K337A/M298Q/E296V-FVII, F374Y/K337A/M298Q/V158D-FVII, F374Y/K337A/E296V/V158D-FVII, F374Y/V158D/S314E/M298Q-FVII, F374Y/V158D/S314E/E296V-FVII, F374Y/V158D/M298Q/E296V-FVII, F374Y/V158T/S314E/E296V-FVII, F374Y/V158T/S314E/M298Q-FVII, F374Y/V158T/M298Q/E296V-FVII, F374Y/E296V/S314E/M298Q-FVII, F374Y/L305V/K337A/S314E-FVII, F374Y/L305V/E296V/K337A/S314E-FVII, F374Y/E296V/M298Q/K337A/S314E-FVII, F374Y/L305V/E296V/M298Q/K337A-FVII, F374Y/L305V/E296V/M298Q/S314E-FVII, F374Y/V158D/E296V/M298Q/K337A-FVII, F374Y/V158D/E296V/M298Q/S314E-FVII, F374Y/L305V/V158D/K337A/S314E-FVII, F374Y/V158D/M298Q/K337A/S314E-FVII, F374Y/V158D/E296V/K337A/S314E-FVII, F374Y/L305V/V158D/E296V/M298Q-FVII, F374Y/L305V/V158D/M298Q/K337A-FVII, F374Y/L305V/V158D/E296V/K337A-FVII, F374Y/L305V/V158D/M298Q/S314E-FVII, F374Y/L305V/V158D/E296V/S314E-FVII, F374Y/V158T/E296V/M298Q/K337A-FVII, F374Y/V158T/E296V/M298Q/S314E-FVII, F374Y/L305V/V158T/K337A/S314E-FVII, F374Y/V158T/M298Q/K337A/S314E-FVII, F374Y/V158T/E296V/K337A/S314E-FVII, F374Y/L305V/V158T/E296V/M298Q-FVII, F374Y/L305V/V158T/M298Q/K337A-FVII, F374Y/L305V/V158T/E296V/K337A-FVII, F374Y/L305V/V158T/M298Q/S314E-FVII, F374Y/L305V/V158T/E296V/S314E-FVII, F374Y/E296V/M298Q/K337A/V158T/S314E-FVII, F374Y/V158D/E296V/M298Q/K337A/S314E-FVII, F374Y/L305V/E296V/M298Q/V158T/S314E-FVII, F374Y/L305V/E296V/M298Q/K337A/V158T-FVII, F374Y/L305V/E296V/K337A/V158T/S314E-FVII, F374Y/L305V/M298Q/K337A/V158T/S314E-FVII, F374Y/L305V/V158D/E296V/M298Q/K337A-FVII, F374Y/L305V/V158D/E296V/K337A/S314E-FVII, F374Y/L305V/V158D/M298Q/K337A/S314E-FVII, F374Y/L305V/E296V/M298Q/K337A/V158T/S314E-FVII, F374Y/L305V/V158D/E296V/M298Q/K337A/S314E-FVII, S52A-Factor VII, S60A-Factor VII; R152E-Factor VII, S344A-Factor VII, Factor VIIa lacking the Gla domain; and P11Q/K33E-FVII, T106N-FVII, K143N/N145T-FVII, V253N-FVII, R290N/A292T-FVII, G291N-FVII, R315N/V317T-FVII, K143N/N145T/R315N/V317T-FVII; and FVII having substitutions, additions or deletions in the amino acid sequence from 233Thr to 240Asn, FVII having substitutions, additions or deletions in the amino acid sequence from 304Arg to 329Cys.

In one embodiment of the invention the molar ratio of calcium ions and Factor VII polypeptide ($Ca^{2+}$:FVII polypeptide) under step (iii) is higher than 20. In one embodiment of the invention the molar ratio of calcium ions and Factor VII polypeptide ($Ca^{2+}$:FVII polypeptide) under step (iii) is higher than 20, such as higher than 22, such as higher than 24, such as higher than 26, such as higher than 28, such as higher than 30, such as higher than 34, such as higher than 38, such as higher than 42, such as higher than 45, such as higher than 50, such as higher than 55, such as higher than 60, such as higher than 65, such as higher than 70, such as higher than 76, such as higher than 82, such as higher than 90, such as higher than 95, such as higher than 100.

In one embodiment of the invention the molar ratio of calcium ions and Factor VII polypeptide ($Ca^{2+}$:FVII polypeptide) under step (iii) is lower than 0.50. In one embodiment of the invention the molar ratio of calcium ions and Factor VII polypeptide ($Ca^{2+}$:FVII polypeptide) under step (iii) is lower than 0.50, such as lower than 0.45, such as lower than 0.40, such as lower than 0.35, such as lower than 0.30, such as lower than 0.25, such as lower than 0.20, such as lower than 0.15, such as lower than 0.10, such as lower than 0.05, such as 0.00.

In one embodiment of the invention the free calcium ion concentration at least in one of the purification steps is higher than 1.2 mM. In one embodiment of the invention the free calcium ion concentration at least in one of the purification steps is higher than 1.3 mM, such as higher than 1.4 mM, such as higher than 1.5 mM, such as higher than 1.6 mM, such as higher than 1.7 mM, such as higher than 1.8 mM, such as higher than 1.9 mM, such as higher than 2.0 mM, such as higher than 2.1 mM, such as higher than 2.2 mM, such as higher than 2.3 mM, such as higher than 2.4 mM, such as higher than 2.5 mM, such as higher than 2.6 mM, such as higher than 3.0 mM, such as higher than 4.0 mM, such as higher than 5.0 mM, such as higher than 6.0 mM, such as higher than 7.0 mM, such as higher than 8.0 mM, such as higher than 9.0 mM, such as higher than 10.0 mM, such as higher than 20 mM, such as higher than 40.0 mM, such as higher than 60.0 mM, such as higher than 80.0 mM, such as higher than 0.1 M, such as higher than 1 M, such as a free calcium ion concentration, where the solution is saturated.

In one embodiment of the invention the free calcium ion concentration at least in one of the purification steps is lower than 0.10 mM. In one embodiment of the invention the free calcium ion concentration at least in one of the purification steps is lower than 0.09, such as lower than 0.08, such as lower than 0.07, such as lower than 0.06, such as lower than 0.05, such as lower than 0.04, such as lower than 0.03, such as lower than 0.02, such as lower than 0.01, such as lower than 0.00.

In one embodiment of the invention the free ion concentration of a divalent metal cation other than a zinc ion and a calcium ion at least in one of the purification steps is higher than 0.025 mM. In one embodiment of the invention the divalent metal cation is selected from the list consisting of $Mg^{2+}$, $Cu^{2+}$, $Mn^{2+}$, $Co^{2+}$, $Fe^{2+}$, $Sm^{2+}$, $Ni^{2+}$, $Cd^{2+}$, $Hg^{2+}$, $Sm^{2+}$, $Uo^{2+}$. In one embodiment of the invention the divalent metal cation is selected from the list consisting of $Mg^{2+}$, $Cu^{2+}$, and $Mn^{2+}$.

In one embodiment of the invention the free ion concentration of a divalent metal cation other than a zinc ion and a calcium ion at least in one of the purification steps is higher than 0.025 mM, such as higher than 0.03 mM, such as higher than 0.035 mM, such as higher than 0.04 mM, such as higher than 0.045 mM, such as higher than 0.05 mM, such as higher than 0.055 mM, such as higher than 0.06 mM, such as higher than 0.1 mM, such as higher than 0.15 mM, such as higher than 0.2 mM, such as higher than 0.25 mM, such as higher than 0.3 mM, such as higher than 0.5 mM, such as higher than 1.0 mM.

In one embodiment of the invention the Factor VII polypeptide is purified at least in one of the purification steps in the presence of a further divalent metal ion chelator.

In one embodiment of the invention the Factor VII polypeptide is purified at least in one of the purification steps at a pH lower than 7.5. In one embodiment of the invention the pH is lower than 7.4, such as lower than 7.3, such as lower than 7.2, such as lower than 7.1, such as lower than 7.0, such as lower than 6.8, such as lower than 6.6, such as lower than 6.4, such as lower than 6.2, such as lower than 6.0, such as 5.5.

In one embodiment of the invention the Factor VII polypeptide is purified at least in one of the purification steps at a pH higher than 8.6. In one embodiment of the invention the pH is higher than 8.7, such as higher than 8.8, such as higher than 8.9, such as higher than 9.0, such as higher than 9.1, such as higher than 9.2, such as higher than 9.4, such as higher than 9.6, such as higher than 9.8, such as higher than 10.0, such as higher than 10.2, such as higher than 10.4, such as higher than 10.8, such as 11.0.

In one embodiment of the invention the Factor VII polypeptide is purified at least in one of the purification steps in the presence of histidine.

In one embodiment of the invention the free calcium ion concentration obtained is higher than 1.2 mM. In one embodiment of the invention the free calcium ion concentration obtained is higher than 1.3 mM, such as higher than 1.4 mM, such as higher than 1.5 mM, such as higher than 1.6 mM, such as higher than 1.7 mM, such as higher than 1.8 mM, such as higher than 1.9 mM, such as higher than 2.0 mM, such as higher than 2.1 mM, such as higher than 2.2 mM, such as higher than 2.3 mM, such as higher than 2.4 mM, such as higher than 2.5 mM, such as higher than 2.6 mM, such as higher than 3.0 mM, such as higher than 4.0 mM, such as higher than 5.0 mM, such as higher than 6.0 mM, such as higher than 7.0 mM, such as higher than 8.0 mM, such as higher than 9.0 mM, such as higher than 10.0 mM, such as higher than 20 mM, such as higher than 40.0 mM, such as higher than 60.0 mM, such as higher than 80.0 mM, such as higher than 0.1 M, such as higher than 1 M, such as a free calcium ion concentration, where the solution is saturated.

In one embodiment of the invention the free calcium ion concentration obtained is lower than 0.10 mM. In one embodiment of the invention the free calcium ion concentration obtained is lower than 0.09, such as lower than 0.08, such as lower than 0.07, such as lower than 0.06, such as lower than 0.05, such as lower than 0.04, such as lower than 0.03, such as lower than 0.02, such as lower than 0.01, such as lower than 0.00.

In one embodiment of the invention the free ion concentration of a divalent metal cation other than a zinc ion and a calcium ion obtained is higher than 0.025 mM.

In one embodiment of the invention the divalent metal cation is selected from the list consisting of $Mg^{2+}$, $Cu^{2+}$, $Mn^{2+}$, $Co^{2+}$, $Fe^{2+}$, $Sm^{2+}$, $Ni^{2+}$, $Cd^{2+}$, $Hg^{2+}$, $Sm^{2+}$, and $Uo^{2+}$. In one embodiment of the invention the divalent metal cation is selected from the list consisting of $Mg^{2+}$, $Cu^{2+}$, and $Mn^{2+}$.

In one embodiment of the invention the free ion concentration of a divalent metal cation other than a zinc ion and a calcium ion obtained is higher than 0.025 mM, such as higher than 0.03 mM, such as higher than 0.035 mM, such as higher than 0.04 mM, such as higher than 0.045 mM, such as higher than 0.05 mM, such as higher than 0.055 mM, such as higher than 0.06 mM, such as higher than 0.1 mM, such as higher than 0.15 mM, such as higher than 0.2 mM, such as higher than 0.25 mM, such as higher than 0.3 mM, such as higher than 0.5 mM, such as higher than 1.0 mM.

In one embodiment of the invention the Factor VII polypeptide is stabilized in the presence of a further divalent metal ion chelator.

In one embodiment of the invention the Factor VII polypeptide is stabilized at a pH lower than 7.5. In one embodiment of the invention the pH is lower than 7.4, such as lower than 7.3, such as lower than 7.2, such as lower than 7.1, such as lower than 7.0, such as lower than 6.8, such as lower than 6.6, such as lower than 6.4, such as lower than 6.2, such as lower than 6.0, such as 5.5. In one embodiment of the invention the Factor VII polypeptide is stabilized at a pH higher than 8.6. In one embodiment of the invention the pH is higher than 8.7, such as higher than 8.8, such as higher than 8.9, such as higher than 9.0, such as higher than 9.1, such as higher than 9.2, such as higher than 9.4, such as higher than 9.6, such as higher than 9.8, such as higher than 10.0, such as higher than 10.2, such as higher than 10.4, such as higher than 10.8, such as 11.0.

In one embodiment of the invention the Factor VII polypeptide is stabilized in the presence of histidine.

The term "Factor IX polypeptide" as used herein, means human wild-type Factor IX as well as variants of Factor IX exhibiting substantially the same or improved biological activity relative to wild-type Factor IX, Factor IX-related polypeptides as well as Factor IX derivatives and Factor IX conjugates. The term "Factor IX" is intended to encompass Factor IX polypeptides in their uncleaved (zymogen) form, as well as those that have been proteolytically processed to yield their respective bioactive forms, which may be designated Factor IXa. Such variants of Factor IX may exhibit different properties relative to human Factor IX, including stability, phospholipid binding, altered specific activity, and the like.

The term "Factor VII polypeptide", as used herein means wild-type Factor VII (i.e., a polypeptide having the amino acid sequence disclosed in U.S. Patent No. 4,784,950)(SEQ ID NO: 1), as well as variants of Factor VII exhibiting substantially the same or improved biological activity relative to wild-type Factor VII, Factor VII-related polypeptides as well as Factor VII derivatives and Factor VII conjugates. The term "Factor VII" is intended to encompass Factor VII polypeptides in their uncleaved (zymogen) form, as well as those that have been proteolytically processed to yield their respective bioactive forms, which may be designated Factor VIIa. Typically, Factor VII is cleaved between residues 152 and 153 to yield Factor VIIa. Such variants of Factor VII may exhibit different properties relative to human Factor VII, including stability, phospholipid binding, altered specific activity, and the like.

As used herein, "Factor VII-related polypeptides" encompasses polypeptides, including variants, in which the Factor VIIa biological activity has been substantially modified or reduced relative to the activity of wild-type Factor VIIa. These polypeptides include, without limitation, Factor VII or Factor VIIa into which specific amino acid sequence alterations have been introduced that modify or disrupt the bioactivity of the polypeptide.

The term "Factor VII derivative" as used herein, is intended to designate wild-type Factor VII, variants of Factor VII exhibiting substantially the same or improved biological activity relative to wild-type Factor VII and Factor VII-related polypeptides, in which one or more of the amino acids of the parent peptide have been chemically modified, e.g. by alkylation, PEGy-lation, acylation, ester formation or amide formation or the like. This includes but are not limited to PEGylated human Factor VIIa, cysteine-PEGylated human Factor VIIa and variants thereof.

The term "PEGylated human Factor VIIa" means human Factor VIIa, having a PEG mole-cule conjugated to a human Factor VIIa polypeptide. It is to be understood, that the PEG molecule may be attached to any part of the Factor VIIa polypeptide including any amino acid residue or carbohydrate moiety of the Factor VIIa polypeptide. The term "cysteine-PEGylated human Factor VIIa" means Factor VIIa having a PEG molecule conjugated to a sulfhydryl group of a cysteine introduced in human Factor VIIa.

The biological activity of Factor VIIa in blood clotting derives from its ability to (i) bind to tissue factor (TF) and (ii) catalyze the proteolytic cleavage of Factor IX or Factor X to produce activated Factor IX or X (Factor IXa or Xa, respectively). For purposes of the invention, Factor VIIa biological activity may be quantified by measuring the ability of a preparation to promote blood clotting using Factor VII-deficient plasma and thromboplastin, as described, e.g., in U.S. Pat. No. 5,997,864. In this assay, biological activity is expressed as the reduction in clotting time relative to a control sample and is converted to "Factor VII units" by comparison with a pooled human serum standard containing 1 unit/ml Factor VII activity. Alternatively, Factor VIIa biological activity may be quantified by (i) measuring the ability of Factor VIIa to produce activated Factor Xa in a system comprising TF embedded in a lipid membrane and Factor X. (Persson et al., J. Biol. Chem. 272:19919-19924, 1997); (ii) measuring Factor X hydrolysis in an aqueous system; (iii) measuring its physical binding to TF using an instrument based on surface plasmon resonance (Persson, FEBS Letts. 413:359-363, 1997) and (iv) measuring hydrolysis of a synthetic substrate.

Factor VII variants having substantially the same or improved biological activity relative to wild-type Factor VIIa encompass those that exhibit at least about 25%, preferably at least about 50%, more preferably at least about 75% and most preferably at least about 90% of the specific activity of Factor VIIa that has been produced in the same cell type, when tested in one or more of a clotting assay, proteolysis assay, or TF binding assay as described above. Factor VII variants having substantially reduced biological activity relative to wild-type Factor VIIa are those that exhibit less than about 25%, preferably less than about 10%, more preferably less than about 5% and most preferably less than about 1% of the specific activity of wild-type Factor VIIa that has been produced in the same cell type when tested in one or more of a clotting assay, proteolysis assay, or TF binding assay as described above. Factor VII variants having a substantially modified biological activity relative to wild-type Factor VII include, without limitation, Factor VII variants that exhibit TF-independent Factor X proteolytic activity and those that bind TF but do not cleave Factor X.

Variants of Factor VII, whether exhibiting substantially the same or better bioactivity than wild-type Factor VII, or, alternatively, exhibiting substantially modified or reduced bioactivity relative to wild-type Factor VII, include, without limitation, polypeptides having amino acid an sequence that differs from the sequence of wild-type Factor VII (SEQ ID NO: 1) by insertion, deletion, or substitution of one or more amino acids.

Non-limiting examples of Factor VII variants having substantially the same biological activity as wild-type Factor VII include S52A-FVIIa, S60A-FVIIa (Lino et al., Arch. Biochem. Biophys. 352: 182-192, 1998); FVIIa variants exhibiting increased proteolytic stability as disclosed in U.S. Pat. No. 5,580,560; Factor VIIa that has been proteolytically cleaved between residues 290 and 291 or between residues 315 and 316 (Mollerup et al., Biotechnol. Bioeng. 48:501-505, 1995); oxidized forms of Factor VIIa (Kornfelt et al., Arch. Biochem. Biophys. 363:43-54, 1999); FVII variants as disclosed in PCT/DK02/00189; and FVII variants exhibiting increased proteolytic stability as disclosed in WO 02/38162 (Scripps Research Institute); FVII variants having a modified Gla-domain and exhibiting an enhanced membrane binding as disclosed in WO 99/20767 (University of Minnesota); and FVII variants as disclosed in WO 01/58935 (Maxygen ApS).

Non-limiting examples of FVII variants having increased biological activity compared to wild-type FVIIa include FVII variants as disclosed in WO 01/83725, WO 02/22776, WO 02/077218, PCT/DK02/00635, Danish patent application PA 2002 01423, Danish patent application PA 2001 01627; WO 02/38162 (Scripps Research Institute); and FVIIa variants with enhanced activity as disclosed in JP 2001061479 (Chemo-Sero-Therapeutic Res Inst.). Non-limiting examples of Factor VII variants having substantially reduced or modified biological activity relative to wild-type Factor VII include R152E-FVIIa (Wildgoose et al., Biochem 29:3413-3420, 1990), S344A-FVIIa (Kazama et al., J. Biol. Chem. 270:66-72, 1995), FFR-FVIIa (Holst et al., Eur. J. Vasc. Endovasc. Surg. 15:515-520, 1998), and Factor VIIa lacking the Gla domain, (Nicolaisen et al., FEBS Letts. 317:245-249, 1993). Examples of factor VII or factor VII-related polypeptides include, without limitation, wild-type Factor VII, L305V-FVII, L305V/M306D/D309S-FVII, L3051-FVII, L305T-FVII, F374P-FVII, V158T/M298Q-FVII, V158D/E296V/M298Q-FVII, K337A-FVII; M298Q-FVII, V158D/M298Q-FVII, L305V/K337A-FVII, V158D/E296V/M298Q/L305V-FVII, V158D/E296V/M298Q/K337A-FVII, V158D/E296V/M298Q/L305V/K337A-FVII, K157A-FVII, E296V-FVII, E296V/M298Q-FVII, V158D/E296V-FVII, V158D/M298K-FVII, and S336G-FVII, L305V/K337A-FVII, L305V/V158D-FVII, L305V/E296V-FVII, L305V/M298Q-FVII, L305V/V158T-FVII, L305V/K337A/V158T-FVII, L305V/K337A/M298Q-FVII, L305V/K337A/E296V-FVII, L305V/K337A/V158D-FVII, L305V/V158D/M298Q-FVII, L305V/V158D/E296V-FVII, L305V/V158T/M298Q-FVII, L305V/V158T/E296V-FVII, L305V/E296V/M298Q-FVII, L305V/V158D/E296V/M298Q-FVII, L305V/V158T/E296V/M298Q-FVII, L305V/V158T/K337A/M298Q-FVII, L305V/V158T/E296V/K337A-FVII, L305V/V158D/K337A/M298Q-FVII, L305V/V158D/E296V/M298Q/K337A-FVII, L305V/V158D/E296V/K337A-FVII, L305V/V158T/E296V/M298Q/K337A-FVII, S314E/K316H-FVII, S314E/K316Q-FVII, S314E/L305V-FVII, S314E/K337A-FVII, S314E/V158D-FVII, S314E/E296V-FVII, S314E/M298Q-FVII, S314E/V158T-FVII, K316H/L305V-FVII, K316H/K337A-FVII, K316H/V158D-FVII, K316H/E296V-FVII, K316H/M298Q-FVII, K316H/V158T-FVII, K316Q/L305V-FVII, K316Q/K337A-FVII, K316Q/V158D-FVII, K316Q/E296V-FVII, K316Q/M298Q-FVII, K316Q/V158T-FVII, S314E/L305V/K337A-FVII, S314E/L305V/V158D-FVII, S314E/L305V/E296V-FVII, S314E/L305V/M298Q-FVII, S314E/L305V/V158T-FVII, S314E/L305V/K337A/V158T-FVII, S314E/L305V/K337A/M298Q-FVII, S314E/L305V/K337A/E296V-FVII, S314E/L305V/K337A/V158D-FVII, S314E/L305V/V158D/M298Q-FVII, S314E/L305V/V158D/E296V-FVII, S314E/L305V/V158T/M298Q-FVII, S314E/L305V/V158T/E296V-FVII, S314E/L305V/E296V/M298Q-FVII, S314E/L305V/V158D/E296V/M298Q-FVII, S314E/L305V/V158T/E296V/M298Q-FVII, S314E/L305V/V158T/K337A/M298Q-FVII, S314E/L305V/V158T/E296V/K337A-FVII, S314E/L305V/V158D/K337A/M298Q-FVII, S314E/L305V/V158D/E296V/K337A-FVII, S314E/L305V/V158D/E296V/M298Q/K337A-FVII, S314E/L305V/V158T/E296V/M298Q/K337A-FVII, K316H/L305V/K337A-FVII, K316H/L305V/V158D-FVII, K316H/L305V/E296V-FVII, K316H/L305V/M298Q-FVII, K316H/L305V/V158T-FVII, K316H/L305V/K337A/ V158T-FVII, K316H/L305V/K337A/M298Q-FVII, K316H/ L305V/K337A/E296V-FVII, K316H/L305V/K337A/ V158D-FVII, K316H/L305V/V158D/M298Q-FVII, K316H/L305V/V158D/E296V-FVII, K316H/L305V/ V158T/M298Q-FVII, K316H/L305V/V158T/E296V-FVII, K316H/L305V/E296V/M298Q-FVII, K316H/L305V/ V158D/E296V/M298Q-FVII, K316H/L305V/V158T/ E296V/M298Q-FVII, K316H/L305V/V158T/K337A/ M298Q-FVII, K316H/L305V/V158T/E296V/K337A-FVII, K316H/L305V/V158D/K337A/M298Q-FVII, K316H/ L305V/V158D/E296V/K337A-FVII, K316H/L305V/ V158D/E296V/M298Q/K337A-FVII, K316H/L305V/ V158T/E296V/M298Q/K337A-FVII, K316Q/L305V/ K337A-FVII, K316Q/L305V/V158D-FVII, K316Q/L305V/ E296V-FVII, K316Q/L305V/M298Q-FVII, K316Q/L305V/ V158T-FVII, K316Q/L305V/K337A/V158T-FVII, K316Q/ L305V/K337A/M298Q-FVII, K316Q/L305V/K337A/ E296V-FVII, K316Q/L305V/K337A/V158D-FVII, K316Q/ L305V/V158D/M298Q-FVII, K316Q/L305V/V158D/ E296V-FVII, K316Q/L305V/V158T/M298Q-FVII, K316Q/ L305V/V158T/E296V-FVII, K316Q/L305V/E296V/ M298Q-FVII, K316Q/L305V/V158D/E296V/M298Q-FVII, K316Q/L305V/V158T/E296V/M298Q-FVII, K316Q/ L305V/V158T/K337A/M298Q-FVII, K316Q/L305V/ V158T/E296V/K337A-FVII, K316Q/L305V/V158D/ K337A/M298Q-FVII, K316Q/L305V/V158D/E296V/ K337A-FVII, K316Q/L305V/V158D/E296V/M298Q/ K337A-FVII, K316Q/L305V/V158T/E296V/M298Q/ K337A-FVII, F374Y/K337A-FVII, F374Y/V158D-FVII, F374Y/E296V-FVII, F374Y/M298Q-FVII, F374Y/V158T-FVII, F374Y/S314E-FVII, F374Y/L305V-FVII, F374Y/ L305V/K337A-FVII, F374Y/L305V/V158D-FVII, F374Y/ L305V/E296V-FVII, F374Y/L305V/M298Q-FVII, F374Y/ L305V/V158T-FVII, F374Y/L305V/S314E-FVII, F374Y/ K337A/S314E-FVII, F374Y/K337A/V158T-FVII, F374Y/ K337A/M298Q-FVII, F374Y/K337A/E296V-FVII, F374Y/ K337V/N1158D-FVII, F374Y/V158D/S314E-FVII, F374Y/V158D/M298Q-FVII, F374Y/V158D/E296V-FVII, F374Y/V158T/S314E-FVII, F374Y/V158T/M298Q-FVII, F374Y/V158T/E296V-FVII, F374Y/E296V/S314E-FVII, F374Y/S314E/M298Q-FVII, F374Y/E296V/M298Q-FVII, F374Y/L305V/K337A/V158D-FVII, F374Y/L305V/ K337A/E296V-FVII, F374Y/L305V/K337A/M298Q-FVII, F374Y/L305V/K337A/V158T-FVII, F374Y/L305V/ K337A/S314E-FVII, F374Y/L305V/V158D/E296V-FVII, F374Y/L305V/V158D/M298Q-FVII, F374Y/L305V/ V158D/S314E-FVII, F374Y/L305V/E296V/M298Q-FVII, F374Y/L305V/E296V/V158T-FVII, F374Y/L305V/E296V/ S314E-FVII, F374Y/L305V/M298Q/V158T-FVII, F374Y/ L305V/M298Q/S314E-FVII, F374Y/L305V/V158T/ S314E-FVII, F374Y/K337A/S314E/V158T-FVII, F374Y/ K337A/S314E/M298Q-FVII, F374Y/K337A/S314E/ E296V-FVII, F374Y/K337A/S314E/V158D-FVII, F374Y/ K337A/V158T/M298Q-FVII, F374Y/K337A/V158T/ E296V-FVII, F374Y/K337A/M298Q/E296V-FVII, F374Y/ K337A/M298Q/V158D-FVII, F374Y/K337A/E296V/ V158D-FVII, F374Y/V158D/S314E/M298Q-FVII, F374Y/ V158D/S314E/E296V-FVII, F374Y/V158D/M298Q/ E296V-FVII, F374Y/V158T/S314E/E296V-FVII, F374Y/ V158T/S314E/M298Q-FVII, F374Y/V158T/M298Q/ E296V-FVII, F374Y/E296V/S314E/M298Q-FVII, F374Y/ L305V/M298Q/K337A/S314E-FVII, F374Y/L305V/ E296V/K337A/S314E-FVII, F374Y/E296V/M298Q/ K337A/S314E-FVII, F374Y/L305V/E296V/M298Q/ K337A-FVII, F374Y/L305V/E296V/M298Q/S314E-FVII, F374Y/V158D/E296V/M298Q/K337A-FVII, F374Y/ V158D/E296V/M298Q/S314E-FVII, F374Y/L305V/ V158D/K337A/S314E-FVII, F374Y/V158D/M298Q/ K337A/S314E-FVII, F374Y/V158D/E296V/K337A/ S314E-FVII, F374Y/L305V/V158D/E296V/M298Q-FVII, F374Y/L305V/V158D/M298Q/K337A-FVII, F374Y/ L305V/V158D/E296V/K337A-FVII, F374Y/L305V/ V158D/M298Q/S314E-FVII, F374Y/L305V/V158D/ E296V/S314E-FVII, F374Y/V158T/E296V/M298Q/ K337A-FVII, F374Y/V158T/E296V/M298Q/S314E-FVII, F374Y/L305V/V158T/K337A/S314E-FVII, F374Y/ V158T/M298Q/K337A/S314E-FVII, F374Y/V158T/ E296V/K337A/S314E-FVII, F374Y/L305V/V158T/ E296V/M298Q-FVII, F374Y/L305V/V158T/M298Q/ K337A-FVII, F374Y/L305V/V158T/E296V/K337A-FVII, F374Y/L305V/V158T/M298Q/S314E-FVII, F374Y/ L305V/V158T/E296V/S314E-FVII, F374Y/E296V/ M298Q/K337A/V158T/S314E-FVII, F374Y/V158D/ E296V/M298Q/K337A/S314E-FVII, F374Y/L305V/ V158D/E296V/M298Q/S314E-FVII, F374Y/L305V/ E296V/M298Q/V158T/S314E-FVII, F374Y/L305V/ E296V/M298Q/K337A/V158T-FVII, F374Y/L305V/ E296V/K337A/V158T/S314E-FVII, F374Y/L305V/ M298Q/K337A/V158T/S314E-FVII, F374Y/L305V/ V158D/E296V/M298Q/K337A-FVII, F374Y/L305V/ V158D/E296V/K337A/S314E-FVII, F374Y/L305V/ V158D/M298Q/K337A/S314E-FVII, F374Y/L305V/ E296V/M298Q/K337A/V158T/S314E-FVII, F374Y/ L305V/V158D/E296V/M298Q/K337A/S314E-FVII, S52A-Factor VII, S60A-Factor VII; R152E-Factor VII, S344A-Factor VII, Factor VIIa lacking the Gla domain; and P11Q/K33E-FVII, T106N-FVII, K143N/N145T-FVII, V253N-FVII, R290N/A292T-FVII, G291N-FVII, R315N/ V317T-FVII, K143N/N145T/R315N/V317T-FVII; and FVII having substitutions, additions or deletions in the amino acid sequence from 233Thr to 240Asn, FVII having substitutions, additions or deletions in the amino acid sequence from 304Arg to 329Cys.

The terminology for amino acid substitutions used are as follows. The first letter represent the amino acid naturally present at a position of human wild type FVII. The following number represent the position in human wild type FVII. The second letter represent the different amino acid substituting for (replacing) the natural amino acid. An example is M298Q, where an methionine at position 298 of human wild type FVII is replaced by a glutamine. In another example, V158T/ M298Q, the valine in position 158 of human wild type FVII is replaced by a threonine and the methionine in position 298 of human wild type FVII is replaced by a Glutamine in the same Factor VII polypeptide.

In a further embodiment of the invention, the factor VII polypeptide is a polypeptide, wherein the ratio between the activity of the Factor VII polypeptide and the activity of the wild type human Factor VIIa is at least about 1.25. In one embodiment the ratio between the activity of the Factor VII polypeptide and the activity of the wild type human Factor VIIa is at least about 2.0. In a further embodiment the ratio between the activity of the Factor VII polypeptide and the activity of the wild type human Factor VIIa is at least about 4.0.

In a further embodiment of the invention, the factor VII polypeptide is a polypeptide, wherein the ratio between the activity of the Factor VII polypeptide and the activity of the wild type human Factor VIIa is at least about 1.25 when tested in a Factor VIIa activity assay. In one embodiment the ratio between the activity of the Factor VII polypeptide and the activity of the wild type human Factor VIIa is at least about 2.0 when tested in a Factor VIIa activity assay. In a further embodiment the ratio between the activity of the Factor VII polypeptide and the activity of the wild type human Factor VIIa is at least about 4.0 when tested in a Factor VIIa activity assay. The Factor VIIa activity may be measured by the assays described under "assays".

In a further embodiment of the invention, the factor VII polypeptide is a polypeptide, wherein the ratio between the activity of the Factor VII polypeptide and the activity of the wild type human Factor VIIa is at least about 1.25 when tested in the "In Vitro Hydrolysis Assay". In one embodiment the ratio between the activity of the Factor VII polypeptide and the activity of the wild type human Factor VIIa is at least about 2.0 when tested in the "In Vitro Hydrolysis Assay". In a further embodiment the ratio between the activity of the Factor VII polypeptide and the activity of the wild type human Factor VIIa is at least about 4.0 when tested in the "In Vitro Hydrolysis Assay".

In a further embodiment of the invention, the factor VII polypeptide is a polypeptide, wherein the ratio between the activity of the Factor VII polypeptide and the activity of the wild type human Factor VIIa is at least about 1.25 when tested in the "In Vitro Proteolysis Assay". In one embodiment the ratio between the activity of the Factor VII polypeptide and the activity of the wild type human Factor VIIa is at least about 2.0 when tested in the "In Vitro Proteolysis Assay". In a further embodiment the ratio between the activity of the Factor VII polypeptide and the activity of the wild type human Factor VIIa is at least about 4.0 when tested in the "In Vitro Proteolysis Assay". In a further embodiment the ratio between the activity of the Factor VII polypeptide and the activity of the wild type human Factor VIIa is at least about 8.0 when tested in the "In Vitro Proteolysis Assay".

The present invention is suitable for Factor VII/VIIa variants with increased activity compared to wild type. Factor VII/VIIa variants with increased activity may be found by testing in suitable assays described in the following. These assays can be performed as a simple preliminary in vitro test. Thus, the section "assays" discloses a simple test (entitled "In Vitro Hydrolysis Assay") for the activity of Factor VIIa variants of the invention. Based thereon, Factor VIIa variants which are of particular interest are such variants where the ratio between the activity of the variant and the activity of wild type Factor VII is above 1.0, e.g. at least about 1.25, preferably at least about 2.0, such as at least about 3.0 or, even more preferred, at least about 4.0 when tested in the "In Vitro Hydrolysis Assay".

The activity of the variants can also be measured using a physiological substrate such as factor X ("In Vitro Proteolysis Assay") (see under "assays"), suitably at a concentration of 100-1000 nM, where the factor Xa generated is measured after the addition of a suitable chromogenic substrate (eg. S-2765). In addition, the activity assay may be run at physiological temperature.

The ability of the Factor VIIa variants to generate thrombin can also be measured in an assay comprising all relevant coagulation factors and inhibitors at physiological concentrations (minus factor VIII when mimicking hemophilia A conditions) and activated platelets (as described on p. 543 in Monroe et al. (1997) Brit. J. Haematol. 99, 542-547 which is hereby incorporated as reference).

The Factor VII polypeptides described herein may be produced by means of recombinant nucleic acid techniques. In general, a cloned wild-type Factor VII nucleic acid sequence is modified to encode the desired protein. This modified sequence is then inserted into an expression vector, which is in turn transformed or transfected into host cells. Higher eukaryotic cells, in particular cultured mammalian cells, are preferred as host cells. The complete nucleotide and amino acid sequences for human Factor VII are known (see U.S. Pat. No. 4,784,950, where the cloning and expression of recombinant human Factor VII is described). The bovine Factor VII sequence is described in Takeya et al., J. Biol. Chem. 263: 14868-14872 (1988)).

The amino acid sequence alterations may be accomplished by a variety of techniques. Modification of the nucleic acid sequence may be by site-specific mutagenesis. Techniques for site-specific mutagenesis are well known in the art and are described in, for example, Zoller and Smith (DNA 3:479-488, 1984) or "Splicing by extension overlap", Horton et al., Gene 77, 1989, pp. 61-68. Thus, using the nucleotide and amino acid sequences of Factor VII, one may introduce the alteration(s) of choice. Likewise, procedures for preparing a DNA construct using polymerase chain reaction using specific primers are well known to persons skilled in the art (cf. PCR Protocols, 1990, Academic Press, San Diego, Calif., USA).

The nucleic acid construct encoding the Factor VII polypeptide of the invention may suitably be of genomic or cDNA origin, for instance obtained by preparing a genomic or cDNA library and screening for DNA sequences coding for all or part of the polypeptide by hybridization using synthetic oligonucleotide probes in accordance with standard techniques (cf. Sambrook et al., Molecular Cloning: A Laboratory Manual, 2nd. Ed. Cold Spring Harbor Laboratory, Cold Spring Harbor, N.Y., 1989).

The nucleic acid construct encoding the Factor VII polypeptide may also be prepared synthetically by established standard methods, e.g. the phosphoamidite method described by Beaucage and Caruthers, Tetrahedron Letters 22 (1981), 1859-1869, or the method described by Matthes et al., EMBO Journal 3 (1984), 801-805. According to the phosphoamidite method, oligonucleotides are synthesised, e.g. in an automatic DNA synthesiser, purified, annealed, ligated and cloned in suitable vectors.

Furthermore, the nucleic acid construct may be of mixed synthetic and genomic, mixed synthetic and cDNA or mixed genomic and cDNA origin prepared by ligating fragments of synthetic, genomic or cDNA origin (as appropriate), the fragments corresponding to various parts of the entire nucleic acid construct, in accordance with standard techniques.

The nucleic acid construct is preferably a DNA construct. DNA sequences for use in producing Factor VII polypeptides according to the present invention will typically encode a pre-pro polypeptide at the amino-terminus of Factor VII to obtain proper posttranslational processing (e.g. gamma-carboxylation of glutamic acid residues) and secretion from the host cell. The pre-pro polypeptide may be that of Factor VII or another vitamin K-dependent plasma protein, such as Factor IX, Factor X, prothrombin, protein C or protein S. As will be appreciated by those skilled in the art, additional modifications can be made in the amino acid sequence of the Factor VII polypeptides where those modifications do not significantly impair the ability of the protein to act as a coagulant. For example, the Factor VII polypeptides can also be modified in the activation cleavage site to inhibit the conversion of zymogen Factor VII into its activated two-chain form, as generally described in U.S. Pat. No. 5,288,629.

Expression vectors for use in expressing Factor VIIa variants will comprise a promoter capable of directing the transcription of a cloned gene or cDNA. Preferred promoters for use in cultured mammalian cells include viral promoters and cellular promoters. Viral promoters include the SV40 promoter (Subramani et al., Mol. Cell. Biol. 1:854-864, 1981) and the CMV promoter (Boshart et al., Cell 41:521-530, 1985). A particularly preferred viral promoter is the major late promoter from adenovirus 2 (Kaufman and Sharp, Mol. Cell. Biol. 2:1304-1319, 1982). Cellular promoters include the mouse kappa gene promoter (Bergman et al., Proc. Natl. Acad. Sci. USA 81:7041-7045, 1983) and the mouse VH promoter (Loh et al., Cell 33:85-93, 1983). A particularly preferred cellular promoter is the mouse metallothionein-I promoter (Palmiter et al., Science 222:809-814, 1983). Expression vectors may also contain a set of RNA splice sites located downstream from the promoter and upstream from the insertion site for the Factor VII sequence itself. Preferred RNA splice sites may be obtained from adenovirus and/or immunoglobulin genes. Also contained in the expression vectors is a polyadenylation signal located downstream of the insertion site. Particularly preferred polyadenylation signals include the early or late polyadenylation signal from SV40 (Kaufman and Sharp, ibid.), the polyadenylation signal from the adenovirus 5 E1b region, the human growth hormone gene terminator (DeNoto et al. Nucl. Acids Res. 9:3719-3730, 1981) or the polyadenylation signal from the human Factor VII gene or the bovine Factor VII gene. The expression vectors may also include a noncoding viral leader sequence, such as the adenovirus 2 tripartite leader, located between the promoter and the RNA splice sites; and enhancer sequences, such as the SV40 enhancer.

Cloned DNA sequences are introduced into cultured mammalian cells by, for example, calcium phosphate-mediated transfection (Wigler et al., Cell 14:725-732, 1978; Corsaro and Pearson, Somatic Cell Genetics 7:603-616, 1981; Graham and Van der Eb, Virology 52d:456-467, 1973) or electroporation (Neumann et al., EMBO J. 1:841-845, 1982). To identify and select cells that express the exogenous DNA, a gene that confers a selectable phenotype (a selectable marker) is generally introduced into cells along with the gene or cDNA of interest. Preferred selectable markers include genes that confer resistance to drugs such as neomycin, hygromycin, and methotrexate. The selectable marker may be an amplifiable selectable marker. A preferred amplifiable selectable marker is a dihydrofolate reductase (DHFR) sequence. Selectable markers are reviewed by Thilly (Mammalian Cell Technology, Butterworth Publishers, Stoneham, Mass., incorporated herein by reference). The person skilled in the art will easily be able to choose suitable selectable markers.

Selectable markers may be introduced into the cell on a separate plasmid at the same time as the gene of interest, or they may be introduced on the same plasmid. If, on the same plasmid, the selectable marker and the gene of interest may be under the control of different promoters or the same promoter, the latter arrangement producing a dicistronic message. Constructs of this type are known in the art (for example, Levinson and Simonsen, U.S. Pat. No. 4,713,339). It may also be advantageous to add additional DNA, known as "carrier DNA," to the mixture that is introduced into the cells. After the cells have taken up the DNA, they are grown in an appropriate growth medium, typically for 1-2 days, to begin expressing the gene of interest. The medium used to culture the cells may be any conventional medium suitable for growing the host cells, such as minimal or complex media containing appropriate supplements. Suitable media are available from commercial suppliers or may be prepared according to published recipes (e.g. in catalogues of the American Type Culture Collection). The media are prepared using procedures known in the art (see, e.g., references for bacteria and yeast; Bennett, J. W. and LaSure, L., editors, More Gene Manipulations in Fungi, Academic Press, CA, 1991). Growth media generally include a carbon source, a nitrogen source, essential amino acids, essential sugars, vitamins, salts, phospholipids, proteins and growth factors. For production of gamma-carboxylated Factor VII polypeptides, the medium will contain vitamin K, preferably at a concentration of about 0.1 mg/ml to about 5 mg/ml. Drug selection is then applied to select for the growth of cells that are expressing the selectable marker in a stable fashion. For cells that have been transfected with an amplifiable selectable marker the drug concentration may be increased to select for an increased copy number of the cloned sequences, thereby increasing expression levels. Clones of stably transfected cells are then screened for expression of the desired Factor VII polypeptide.

Preferred mammalian cell lines include the CHO (ATCC CCL 61), COS-1 (ATCC CRL 1650), baby hamster kidney (BHK) and 293 (ATCC CRL 1573; Graham et al., J. Gen. Virol. 36:59-72, 1977) cell lines. A preferred BHK cell line is the tk– ts13 BHK cell line (Waechter and Baserga, Proc. Natl. Acad. Sci. USA 79:1106-1110, 1982), hereinafter referred to as BHK 570 cells. The BHK 570 cell line is available from the American Type Culture Collection, 12301 Parklawn Dr., Rockville, Md. 20852, under ATCC accession number CRL 10314. A tk– ts13 BHK cell line is also available from the ATCC under accession number CRL 1632. In addition, a number of other cell lines may be used, including Rat Hep I (Rat hepatoma; ATCC CRL 1600), Rat Hep II (Rat hepatoma; ATCC CRL 1548), TCMK (ATCC CCL 139), Human lung (ATCC HB 8065), NCTC 1469 (ATCC CCL 9.1) and DUKX cells (Urlaub and Chasin, Proc. Natl. Acad. Sci. USA 77:4216-4220, 1980).

Transgenic animal technology may be employed to produce the Factor VII polypeptides of the invention. It is preferred to produce the proteins within the mammary glands of a host female mammal. Expression in the mammary gland and subsequent secretion of the protein of interest into the milk overcomes many difficulties encountered in isolating proteins from other sources. Milk is readily collected, available in large quantities, and biochemically well characterized. Furthermore, the major milk proteins are present in milk at high concentrations (typically from about 1 to 15 g/l).

From a commercial point of view, it is clearly preferable to use as the host a species that has a large milk yield. While smaller animals such as mice and rats can be used (and are preferred at the proof of principle stage), it is preferred to use livestock mammals including, but not limited to, pigs, goats, sheep and cattle. Sheep are particularly preferred due to such factors as the previous history of transgenesis in this species, milk yield, cost and the ready availability of equipment for collecting sheep milk (see, for example, WO 88/00239 for a comparison of factors influencing the choice of host species). It is generally desirable to select a breed of host animal that has been bred for dairy use, such as East Friesland sheep, or to introduce dairy stock by breeding of the transgenic line at a later date. In any event, animals of known, good health status should be used.

To obtain expression in the mammary gland, a transcription promoter from a milk protein gene is used. Milk protein genes include those genes encoding caseins (see U.S. Pat. No. 5,304,489), beta lactoglobulin, a lactalbumin, and whey acidic protein. The beta lactoglobulin (BLG) promoter is preferred. In the case of the ovine beta lactoglobulin gene, a region of at least the proximal 406 bp of 5' flanking sequence of the gene will generally be used, although larger portions of the 5' flanking sequence, up to about 5 kbp, are preferred, such as a ~4.25 kbp DNA segment encompassing the 5' flanking promoter and non coding portion of the beta lactoglobulin gene (see Whitelaw et al., Biochem. J. 286: 31 39 (1992)).

Similar fragments of promoter DNA from other species are also suitable.

Other regions of the beta lactoglobulin gene may also be incorporated in constructs, as may genomic regions of the gene to be expressed. It is generally accepted in the art that constructs lacking introns, for example, express poorly in comparison with those that contain such DNA sequences (see Brinster et al., Proc. Natl. Acad. Sci. USA 85: 836 840 (1988); Palmiter et al., Proc. Natl. Acad. Sci. USA 88: 478 482 (1991); Whitelaw et al., Transgenic Res. 1: 3 13 (1991); WO 89/01343; and WO 91/02318, each of which is incorporated herein by reference). In this regard, it is generally preferred, where possible, to use genomic sequences containing all or some of the native introns of a gene encoding the protein or polypeptide of interest, thus the further inclusion of at least some introns from, e.g, the beta lactoglobulin gene, is preferred. One such region is a DNA segment that provides for intron splicing and RNA polyadenylation from the 3' non coding region of the ovine beta lactoglobulin gene. When substituted for the natural 3' non coding sequences of a gene, this ovine beta lactoglobulin segment can both enhance and stabilize expression levels of the protein or polypeptide of interest. Within other embodiments, the region surrounding the initiation ATG of the variant Factor VII sequence is replaced with corresponding sequences from a milk specific protein gene. Such replacement provides a putative tissue specific initiation environment to enhance expression. It is convenient to replace the entire variant Factor VII pre pro and 5' non coding sequences with those of, for example, the BLG gene, although smaller regions may be replaced.

For expression of Factor VII polypeptides in transgenic animals, a DNA segment encoding variant Factor VII is operably linked to additional DNA segments required for its expression to produce expression units. Such additional segments include the above mentioned promoter, as well as sequences that provide for termination of transcription and polyadenylation of mRNA. The expression units will further include a DNA segment encoding a secretory signal sequence operably linked to the segment encoding modified Factor VII. The secretory signal sequence may be a native Factor VII secretory signal sequence or may be that of another protein, such as a milk protein (see, for example, von Heijne, Nucl. Acids Res. 14: 4683 4690 (1986); and Meade et al., U.S. Pat. No. 4,873,316, which are incorporated herein by reference).

Construction of expression units for use in transgenic animals is conveniently carried out by inserting a variant Factor VII sequence into a plasmid or phage vector containing the additional DNA segments, although the expression unit may be constructed by essentially any sequence of ligations. It is particularly convenient to provide a vector containing a DNA segment encoding a milk protein and to replace the coding sequence for the milk protein with that of a variant Factor VII polypeptide; thereby creating a gene fusion that includes the expression control sequences of the milk protein gene. In any event, cloning of the expression units in plasmids or other vectors facilitates the amplification of the variant Factor VII sequence. Amplification is conveniently carried out in bacterial (e.g. *E. coli*) host cells, thus the vectors will typically include an origin of replication and a selectable marker functional in bacterial host cells. The expression unit is then introduced into fertilized eggs (including early stage embryos) of the chosen host species. Introduction of heterologous DNA can be accomplished by one of several routes, including microinjection (e.g. U.S. Pat. No. 4,873,191), retroviral infection (Jaenisch, Science 240: 1468 1474 (1988)) or site directed integration using embryonic stem (ES) cells (reviewed by Bradley et al., Bio/Technology 10: 534 539 (1992)). The eggs are then implanted into the oviducts or uteri of pseudopregnant females and allowed to develop to term. Offspring carrying the introduced DNA in their germ line can pass the DNA on to their progeny in the normal, Mendelian fashion, allowing the development of transgenic herds. General procedures for producing transgenic animals are known in the art (see, for example, Hogan et al., Manipulating the Mouse Embryo: A Laboratory Manual, Cold Spring Harbor Laboratory, 1986; Simons et al., Bio/Technology 6: 179 183 (1988); Wall et al., Biol. Reprod. 32: 645 651 (1985); Buhler et al., Bio/Technology 8: 140 143 (1990); Ebert et al., Bio/Technology 9: 835 838 (1991); Krimpenfort et al., Bio/Technology 9: 844 847 (1991); Wall et al., J. Cell. Biochem. 49: 113 120 (1992); U.S. Pat. No. 4,873,191; U.S. Pat. No. 4,873,316; WO 88/00239, WO 90/05188, WO 92/11757; and GB 87/00458). Techniques for introducing foreign DNA sequences into mammals and their germ cells were originally developed in the mouse (see, e.g., Gordon et al., Proc. Natl. Acad. Sci. USA 77: 7380 7384 (1980); Gordon and Ruddle, Science 214: 1244 1246 (1981); Palmiter and Brinster, Cell 41: 343 345 (1985); Brinster et al., Proc. Natl. Acad. Sci. USA 82: 4438 4442 (1985); and Hogan et al. (ibid.)). These techniques were subsequently adapted for use with larger animals, including livestock species (see, e.g., WO 88/00239, WO 90/05188, and WO 92/11757; and Simons et al., Bio/Technology 6: 179 183 (1988)). To summarise, in the most efficient route used to date in the generation of transgenic mice or livestock, several hundred linear molecules of the DNA of interest are injected into one of the pro nuclei of a fertilized egg according to established techniques. Injection of DNA into the cytoplasm of a zygote can also be employed.

Production in transgenic plants may also be employed. Expression may be generalised or directed to a particular organ, such as a tuber (see, Hiatt, Nature 344:469 479 (1990); Edelbaum et al., J. Interferon Res. 12:449 453 (1992); Sijmons et al., Bio/Technology 8:217 221 (1990); and EP 0 255 378).

The Factor VII polypeptides of the invention are recovered from cell culture medium or milk. The Factor VII polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing (IEF), differential solubility (e.g., ammonium sulfate precipitation), or extraction (see, e.g., Protein Purification, J.-C. Janson and Lars Ryden, editors, VCH Publishers, New York, 1989). Preferably, they may be purified by affinity chromatography on an anti-Factor VII antibody column. The use of calcium-dependent monoclonal antibodies is described by Wakabayashi et al., J. Biol. Chem. 261:11097-11108, (1986) and Thim et al., Biochemistry 27: 7785-7793, (1988). Additional purification may be achieved by conventional chemical purification means, such as high performance liquid chromatography. Other methods of purification, including barium citrate precipitation, are known in the art, and may be applied to the purification of the novel Factor VII polypeptides described herein (see, for example, Scopes, R., Protein Purification, Springer-Verlag, N.Y., 1982).

For therapeutic purposes it is preferred that the Factor VII polypeptides of the invention are substantially pure. Thus, in a preferred embodiment of the invention the Factor VII polypeptides of the invention is purified to at least about 90 to 95% homogeneity, preferably to at least about 98% homogeneity. Purity may be assessed by e.g. gel electrophoresis and amino-terminal amino acid sequencing.

The Factor VII polypeptide is cleaved at its activation site in order to convert it to its two-chain form. Activation may be carried out according to procedures known in the art, such as those disclosed by Osterud, et al., Biochemistry 11:2853-2857 (1972); Thomas, U.S. Pat. No. 4,456,591; Hedner and Kisiel, J. Clin. Invest. 71:1836-1841 (1983); or Kisiel and Fujikawa, Behring Inst. Mitt. 73:29-42 (1983). Alternatively, as described by Bjoern et al. (Research Disclosure, 269 September 1986, pp. 564-565), Factor VII may be activated by passing it through an ion-exchange chromatography column, such as Mono Q (Pharmacia fine Chemicals) or the like. The resulting activated Factor VII polypeptide may then be formulated and administered as described below.

Assays

In Vitro Hydrolysis Assay

Wild type (native) Factor VIIa and Factor VIIa variant (both hereafter referred to as "Factor VIIa") are assayed in parallel to directly compare their specific activities. The assay is carried out in a microtiter plate (MaxiSorp, Nunc, Denmark). The chromogenic substrate D-Ile-Pro-Arg-p-nitroanilide (S-2288, Chromogenix, Sweden), final concentration 1 mM, is added to Factor VIIa (final concentration 100 nM) in 50 mM Hepes, pH 7.4, containing 0.1 M NaCl, 5 mM $CaCl_2$ and 1 mg/ml bovine serum albumin. The absorbance at 405 nm is meas-ured continuously in a SpectraMax® 340 plate reader (Molecular Devices, USA). The absorbance developed during a 20-minute incubation, after subtraction of the absorbance in a blank well containing no enzyme, is used to calculate the ratio between the activities of vari-ant and wild-type Factor VIIa:

Ratio=(A405 nm Factor VIIa variant)/(A405 nm Factor VIIa wild-type).

In Vitro Proteolysis Assay

Wild type (native) Factor VIIa and Factor VIIa variant (both hereafter referred to as "Factor VIIa") are assayed in parallel to directly compare their specific activities. The assay is carried out in a microtiter plate (MaxiSorp, Nunc, Denmark). Factor VIIa (10 nM) and Factor X (0.8 microM) in 100 microL 50 mM Hepes, pH 7.4, containing 0.1 M NaCl, 5 mM $CaCl_2$ and 1 mg/ml bovine serum albumin, are incubated for 15 min. Factor X cleavage is then stopped by the addition of 50 microL 50 mM Hepes, pH 7.4, containing 0.1 M NaCl, 20 mM EDTA and 1 mg/ml bovine serum albumin. The amount of Factor Xa generated is measured by addition of the chromogenic substrate Z-D-Arg-Gly-Arg-p-nitroanilide (S-2765, Chromogenix, Swe-den), final concentration 0.5 mM. The absorbance at 405 nm is measured continuously in a SpectraMax® 340 plate reader (Molecular Devices, USA). The absorbance developed dur-ing 10 minutes, after subtraction of the absorbance in a blank well containing no FVIIa, is used to calculate the ratio between the proteolytic activities of variant and wild-type Factor VIIa:

Ratio=($A$405 nm Factor VIIa variant)/($A$405 nm Factor VIIa wild-type).

GD-FVIIa Formation Velocity Assay

GD-FVIIa (GLA domainless FVIIa, 39-406 fragment) formation velocity is determined as the increase in relative GD-FVIIa content over a given period of time. A FVIIa solution of which the GD-FVIIa formation velocity is to be determined is sampled two time. One initial sample and one after incubation at the circumstances to be investigated (pH, concentration, tempoerature etc.). Immedeately after the samples are taken, they are boiled with sample buffer in order to stop any further degradation during analysis. The two samples were analyzed by non-reducing SDS-PAGE and the area of the GD-FVIIa band is measured relative to the FVIIa. The increase in GD-FVIIa content during the incubation in the time between the initial and final samples can then be divided by the incubation time to give the GD-FVIIa formation velocity. SDS-PAGE was performed on samples with an approximate FVIIa concentration of 1 mg/ml, which were mixed with an equal amount of loading buffer and boiled for five minutes. The sample was transfered to a sample well in an 12% NuPAGE Bis-Tris in a MOPS running buffer. An electrical field was applied until the sample front had migrated to the bottom of the gel. The gel casette was taken apart, the gel moved and transferred to fixation, coomassie staining solution and finally destaining solution before the gel was dried.

A 1.3 mg/ml FVIIa solution in a buffer consisting of 125 micromolar $CaCl_2$, 75 mM NaCl, 10 mM glycylclycine, pH 8.6 had an initial GD-FVIIa content of 10% after incubation for 24 hours, the GD-FVIIa content had increased to 70%. Hence the formation velocity was determined to 60% GD-FVIIa/24 hr. A similar sample with a $CaCl_2$ concentration of 2.5 mM, displayed an increase in GD-FVIIa content from 6.6% to 8.2% during 24 hours, yielding a GD-FVIIa formation velocity of 1.6% GD-FVIIa/24 hr.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

The present invention is further described by the following examples which should not be construed as limiting the scope of the invention.

EXAMPLES

In the following examples it is to be understood, that the process may be used for any FVII polypeptide according to the present invention. It further understood that the steps performed in example 2 to example 19 may be combined in arbitrary order to obtain a certain purity of the FVII polypeptide.

Example 1

Stabilizing a Cell Culture Harvest by Adjustment to 200 micromolar $Cu^{2+}$

A 500 ml portion of BHK-21 cell culture supernatant with a FVIIa analogue concentration of 20 mg/l was filtered through a dead-end 0.45 micron filter. The harvest containing a free $Ca^{2+}$ concentration of 2 mM was further stabilized by the addition of a Cobber(II)nitrate solution to a concentration of 200 micromolar $Cu^{2+}$. The stabilized culture supernatant was stored at 5 degrees Celsius before further processing.

Example 2

Purification of FVII Polypeptide by HIC in Presence of $Cu^{2+}$ and Elution Under Low pH Conditions.

Hydrophobic interaction chromatography (HIC) was performed on a column (1 cm inner diameter×7 cm length=5.5 ml) packed with Toyopearl MD-G Butyl resin. The column was equilibrated with 10 CV's of 35 mM $CaCl_2$, 0.1 mM $Cu(NO_3)_2$*$3H_2O$, 1.5 M NaCl, 10 mM tris, pH 7.5. After equilibration, 42 ml of a solution containing 0.1 mg/ml FVIIa was loaded onto the column. After loading, the column was washed with 10 CV's of the equilibration buffer. The bound FVII(a) was eluted using 20 mM EDTA, 50 mM histidine, pH 6.0.

Example 3

Performing Size Exclusion Chromatography in the Presence of $Cu^{2+}$.

Size exclusion chromatography was performed on a 3 ml sample (1 mg/ml) of a hyperactive FVIIa analogue in a pH 6.0 histidine buffered solution. The sample was filtered through a 1 micron dead-end filter before it was applied onto a Toyopearl HW-55F (1 cm inner diameter×100 cm length=79 ml CV) equilibrated in a buffer composed of 50 mM NaCl, 0.1 mM Cobber(II)nitrate, 10 mM histidine, pH 6.0. The running buffer was identical to the equilibration buffer. All segments of the purification were carried out at a flowrate of 12 cm/hr and a temperature of 5 degrees Celsius.

Example 4

Stabilizing a Cell Culture Harvest by Adjusting to pH 6.

A 500 ml portion of CHO K1 cell culture supernatant with a FVIIa analogue concentration of 50 mg/l was stabilized by adding histidine to a concentration of 20 mM followed by adjustment of pH to 6.0. The stabilized culture supernatant was filtered through a dead-end 0.45 micron filter and stored at 5 degrees Celsius before further processing.

Example 5

Performing Anion Exchange Chromatography at pH 6.

Anion exchange chromatography was performed on a column (1 cm inner diameter×10 cm length=7,85 ml column volume(CV)) packed with Pharmacia Q-Sepharose Fast Flow, equilibrated with 5 CV of a solution containing 5 mM EDTA, 10 mM histidine, pH 6.0. The load was 40 CVs of a filtered solution containing 1 mg/ml FVIIa analog, followed by a 5 CV wash using 50 mM NaCl, 10 mM histidine, pH 6.0. The elution was performed using a 40 CV NaCl gradient from 50 mM NaCl to 750 mM NaCl, buffered at pH 6.0 by 10 mM histidine. The entire purification was carried out at a flowrate of 20 CV/h and a temperature of 5 degrees Celsius.

Example 6

Performing Anion Exchange Chromatography at pH 9.

Anion exchange chromatography was performed on a column (1 cm inner diameter x 10 cm length=7,85 ml column volume(CV)) packed with Pharmacia Q-Sepharose Fast Flow, equilibrated with 5 CV of a solution containing 5 mM EDTA, 10 mM histidine, pH 9.0. The load was 40 CVs of a filtered solution containing 1 mg/ml FVIIa analog, followed by a 5 CV wash using 50 mM NaCl, 10 mM histidine, pH 9.0. The elution was performed using a 40 CV NaCl gradient from 50 mM NaCl to 750 mM NaCl, buffered at pH 9.0 by 10 mM histidine. The entire purification was carried out at a flowrate of 20 CV/h and a temperature of 5 degrees Celsius.

Example 7

Performing Size Exclusion Chromatography at pH 6.

Size exclusion chromatography was performed on a 1,5 ml sample (1 mg/ml) of a hyperactive FVIIa analogue in a pH 6.0 histidine buffered solution. The sample was filtered through a 0.45 micron dead-end filter before it was applied onto a Pharmacia superdex 200 column (1 cm inner diameter×60 cm length=47 ml CV) equilibrated in a buffer composed of 50 mM NaCl, 10 mM $CaCl_2$, 10 mM histidine, pH 6.0. The running buffer was identical to the equilibration buffer. All segments of the purification were carried out at a flowrate of 0.3 CV/hr and a temperature of 5 degrees Celsius.

Example 8

Performing Size Exclusion Chromatography at pH 9.

Size exclusion chromatography was performed on a 1,5 ml sample (1 mg/ml) of a hyperactive FVIIa analogue in a pH 9.0 histidine buffered solution. The sample was filtered through a 0.45 micron dead-end filter before it was applied onto a Pharmacia superdex 200 column (1 cm inner diameter×60 cm length=47 ml CV) equilibrated in a buffer composed of 50 mM NaCl, 10 mM $CaCl_2$, 10 mM histidine, pH 9.0. The running buffer was identical to the equilibration buffer. All segments of the purification were carried out at a flowrate of 0.3 CV/hr and a temperature of 5 degrees Celsius.

Example 9

Performing Ultra Filtration at pH 6.

Ultra filtration of HEK293 culture supernatant containing a hyperactive FVIIa analogue was carried out on a Millipore lab scale Tangential Flow Filtration (TFF) system using a 50 cm2 30 kDa Biomax filtration cassette. The dead-end filtrated harvest was stabilized by adding histidine to a concentration of 20 mM and adjustment of pH to 6.0. 500 grams of dead-end filtrated and stabilized harvest was ultra filtrated at a transmembrane pressure (TMP) of 2 bars until a final retentate mass of approx. 25 g, which equals a 20-fold concentration of hyperactive FVIIa analogue, was achieved. The entire process took place at ambient temperature (20 degrees Celsius).

Example 10

Performing Immunoaffinity Purification at pH 6.

A 1500 ml portion of HEK293 culture supernatant was stabilized by the addition of calcium to a concentration of 10 mM $Ca^{2+}$ and by the addition of histidine buffer to a concentration of 10 mM, adjusted with HCl to pH 6.0 and filtered through a 0.45 micron dead-end filter. The stabilized culture supernatant was loaded onto a column (1.6 cm inner diameter×10 cm length=20 ml CV) packed with a $Ca^{2+}$-dependent anti-FVIIa monoclonal antibody, immobilized onto Pharmacia Sepharose 4B. Prior to loading, the column was equilibrated with 5 CV's of 10 mM $CaCl_2$, 10 mM histidine, pH 6.0. After loading, the column was washed with 2 M NaCl, 10 mM $CaCl_2$, 10 mM histidine, pH 6.0 for 10 CV's. The bound FVII(a) was eluted with 10 CV's of 30 mM EDTA, 50 mM histidine, pH 6.0. A flowrate of 12 CV/h and a temperature of 5 degrees Celsius was used throughout the purification.

Example 11

Performing Immunoaffinity Purification at pH 9.

A 1500 ml portion of HEK293 culture supernatant was stabilized by the addition of calcium to a concentration of 10 mM $Ca^{2+}$ and by the addition of histidine buffer to a concentration of 10 mM, adjusted with HCl to pH 9.0 and filtered through a 0.45 micron dead-end filter. The stabilized culture supernatant was loaded onto a column (1.6 cm inner diameter×10 cm length=20 ml CV) packed with a $Ca^{2+}$-dependent anti-FVIIa monoclonal antibody, immobilized onto Pharmacia Sepharose 4B. Prior to loading, the column was equilibrated with 5 CV's of 10 mM $CaCl_2$, 10 mM histidine, pH 9.0. After loading, the column was washed with 2 M NaCl, 10 mM $CaCl_2$, 10 mM histidine, pH 9.0 for 10 CV's. The bound FVII(a) was eluted with 10 CV's of 30 mM EDTA, 50 mM histidine, pH 9.0. A flowrate of 12 CV/h and a temperature of 5 degrees Celsius was used throughout the purification.

Example 12

Stabilizing a Cell Culture Harvest by Adjustment of the $Ca^{2+}$ Concentration to 10 mM A 450 ml portion of HEK293 cell culture supernatant containing a FVIIa analogue concentration of 50 mg/ml and a calcium ion concentration of approximately 2 mM was stabilized by the addition of a $CaCl_2$ solution to a final concentration of 10 mM $Ca^{2+}$. The solution was filtered through a 0.45 micron dead-end filter and was stored at 5 degrees Celsius before further processing.

Example 13

Performing Ultra and Diafiltration in the Presence of 20 mM $Ca^{2+}$

Ultra filtration of a hyperactive FVIIa analogue was carried out on a Millipore lab scale Tangential Flow Filtration (TFF) system using a 50 $cm^2$ 30 kDa Biomax filtration cassette. The FVIIa analogue eluate was stabilized by adding a calcium solution to a concentration of 20 mM $Ca^{2+}$, histidine to a concentration of 10 mM and adjustment of pH to 6.0. 400 grams of stabilized FVIIa analogue was ultra filtrated at a trans-membrane pressure (TMP) of 2 bars until a final retentate mass of approx. 25 g, which equals a 16-fold concentration. Ultra filtration was followed by a three volume turnover diafiltration with a 20 mM $CaCl_2$, 10 mM histidine, pH 6.0 buffer. The same TMP was used for both operations. The entire process took place at ambient temperature (20 degrees Celsius).

Example 14

Performing Immunoaffinity Purification in the Presence of 20 mM $Ca^{2+}$

A 1000 ml portion of BHK-21 culture supernatant, stabilized by the addition of calcium to a concentration of 10 mM $Ca^{2+}$ and by the addition of tris buffer to a concentration of 10 mM and subsequent adjustment with HCl to pH 8 was filtered through a 0.45 micron dead-end filter. The stabilized culture supernatant was loaded onto a column (1.6 cm inner diameter×10 cm length=20 ml CV) packed with a $Ca^{2+}$-dependent anti-FVIIa monoclonal antibody, immobilized onto Pharmacia Sepharose 4B. Prior to loading, the column was equilibrated with 5 CV's of 10 mM $CaCl_2$, 10 mM tris, pH 8. After loading, the column was washed with 2 M NaCl, 10 mM $CaCl_2$, 10 mM tris, pH 8 for 10 CV's. The bound FVII(a) was eluted with 10 CV's of 30 mM EDTA, 50 mM tris, pH 8. A flowrate of 12 CV/h and a temperature of 5 degrees Celsius was used throughout the purification. The eluate was immediately stabilized by the addition of calcium chloride to a final concentration of 50 mM.

Example 15

Performing Immunoaffinity Purification with Load and Wash in the Presence of 20 mM $Ca^{2+}$ Followed by Elution at pH 6.

A 800 ml portion of CHO K1 culture supernatant was stabilized by the addition of calcium to a concentration of 10 mM $Ca^{2+}$. Subsequently, it was added tris buffer to a concentration of 10 mM, adjusted with HCl to pH 7.5 and filtered through a 0.45 micron dead-end filter. The stabilized culture supernatant was loaded onto a column (1.6 cm inner diameter×2 cm length=4 ml CV) packed with a $Ca^{2+}$-dependent anti-FVIIa monoclonal antibody, immobilized onto Pharmacia Sepharose 4B. Prior to loading, the column was equilibrated with 5 CV's of 10 mM $CaCl_2$, 10 mM tris, pH 7.5. After loading, the column was washed with 2 M NaCl, 10 mM $CaCl_2$, 10 mM tris, pH 7.5 for 10 CV's, followed by a second wash containing 2 M NaCl, 10 mM $CaCl_2$, 10 mM histidine, pH 6.0 for 10 CV's The bound FVII(a) was eluted with 10 CV's of 30 mM EDTA, 50 histidine, pH 6.0. A flowrate of 12 CV/h and a temperature of 5 degrees Celsius was used throughout the purification.

Example 16

Performing Size Exclusion Chromatography in the Presence of $Ca^{2+}$

Size exclusion chromatography was performed on a 5 ml sample (1 mg/ml) of a hyperactive FVIIa analogue in a pH 6.0 histidine buffered solution. The sample was filtered through a 1 micron dead-end filter before it was applied onto a Pharmacia Superdex 200 (1 cm inner diameter×80 cm length=63 ml CV) equilibrated in a buffer composed of 50 mM NaCl, 35 mM $CaCl_2$, 10 mM histidine, pH 6.0. The running buffer was identical to the equilibration buffer. All segments of the purification were carried out at a flowrate of 15 cm/hr and a temperature of 5 degrees Celsius.

Example 17

Performing Ultra Filtration and Diafiltration at pH 6 with a High $Ca^{2+}$ Concentration Ultra filtration of HEK293 culture supernatant containing a hyperactive FVIIa analogue was carried out on a Millipore lab scale Tangential Flow Filtration (TFF) system using a 50 cm2 30 kDa Biomax filtration cassette. The dead-end filtrated harvest was stabilized by adding histidine to a concentration of 20 mM and adjustment of pH to 6.0. 500 grams of dead-end filtrated and stabilized harvest was added calcium to a concentration of 35 mM and ultra filtrated at a trans-membrane pressure (TMP) of 2 bars until a final retentate mass of approx. 25 g, which equals a 20-fold concentration of hyperactive FVIIa analogue, was achieved. Ultra filtration was followed by a three volume turnover diafiltration with a 35 mM $CaCl_2$, 10 mM histidine, pH 6.0 buffer. The same TMP was used for both operations. The entire process took place at ambient temperature (20 degrees Celsius).

Example 18

Stabilization of Harvests Using Both Adjustment to pH 6 and Addition of $Cu^{2+}$ A 500 ml portion of CHO-K1 cell culture supernatant with a FVIIa analogue concentration of 50 mg/l was filtered through a dead-end 0.45 micron filter. The harvest containing 2 mM $Ca^{2+}$ was added histidine to a concentration of 10 mM followed by pH adjustment with HCl to pH 6.0. The harvest was further stabilized by the addition of a cobber(II) nitrate solution to a concentration of 200 micromolar $Cu^{2+}$. The stabilized culture supernatant was stored at 5 degrees Celsius before further processing.

Example 19

Stabilization of Harvests Using Both Adjustment to pH 6 and Addition of $Ca^{2+}$ A 1000 ml portion of HEK293 cell culture supernatant containing a FVIIa analogue concentration of 50 mg/ml and a calcium ion concentration of approximately 2 mM was stabilized by the addition of a $CaCl_2$ solution to a final concentration of 10 mM $Ca^{2+}$. Histidine was added to a concentration of 10 mM followed by pH adjustment with HCl to pH 6.0. The solution was filtered through a 0.45 micron dead-end filter and was stored at 5 degrees Celsius before further processing.

Example 20

The effect of $Cu^{2+}$ on the stability of FVII polypeptide is tested in an experiment in which purified FVII polypeptide is adsorbed on Q-Sepharose FF matrix in presence of varying concentrations of $Cu^{2+}$. 500 µg FVII polypeptide is incubated with 50 µl Q-Sepharose FF in 800 µl buffer: 10 mM Tris, 50 mM NaCl, 2 mM $CaCl_2$ and varying concentrations of Cobber(II) nitrate in 1.5 ml test tubes. After 1 hr and 2 hr the matrix is settled by centrifugation and the supernatant removed. 800 µl buffer 10 mM Tris, 50 mM NaCl, 25 mM $CaCl_2$ pH 8.0 is added and after mixing and centrifugation samples of the supernatant is withdrawn and analyzed for by SDS-PAGE.

Example 21

The Purification and Activation of FVII Polypeptide are Performed Through the Following Four Chromatographic Steps:

Step 1:
FVII polypeptide containing cell culture medium is adjusted to ion strength below 10 mS/cm by dilution and applied to a Q-Sepharose column pre-equilibrated with buffer A: 10 mM trihydroxymethylaminomethan (Tris); 150 mM NaCl pH 8.

After a washing step with 175 mM NaCl in the same buffer, FVII polypeptide is eluted by buffer B: 10 mM Tris; 150 mM NaCl; 25 mM $CaCl_2$ pH 8.

Step 2:
The eluate solution containing 104 mg/l FVII polypeptide is adjusted to a final composition: 10 mM Tris; 1M NaCl; 25 mM $CaCl_2$; 70 µM Cobber(II)nitrate pH 7.5 and applied to a Sepharose column with immobilized anti-FVII monoclonal antibody.

The antibody column is pre-equilibrated with buffer C: 10 mM Tris; 100 mM NaCl; 20 mM $CaCl_2$; 70 µM Cobber(II) nitrate pH 7.5. The column is then washed with 10 mM Tris; 2 M NaCl; 20 mM $CaCl_2$; 70 µM Cobber(II)nitrate pH 7.5 followed by buffer C. Thereafter FVII polypeptide is eluted by applying a buffer: 75 mM Tris; 30 mM trisodiumcitrate; 70 µM Cobber(II)nitrate pH 7.5.

Step 3:
The eluate is immediately applied to a Q-Sepharose column pre-equilibrated with buffer: 10 mM Tris; 150 mM NaCl; 70 µM Cobber(II)nitrate pH 8.6.

The column is washed with the same buffer and FVII polypeptide is eluted in a linear gradient from buffer A to buffer D: 10 mM Tris; 500 mM NaCl; 70 µM Cobber(II) nitrate pH 8.6.

Step 4:
The fraction containing FVII polypeptide is adjusted to an ion strength below 10 mS/cm by dilution and immediately applied to a Q-Sepharose column pre-equilibrated with buffer: 10 mM glycylglycine; 150 mM NaCl; 70 µM Cobber (II)nitrate pH 8.6.

After washing with buffer: 10 mM glycylglycine; 175 mM NaCl; 70 µM Cobber(II)nitrate pH 8.6; and buffer E: 10 mM glycylglycine; 100 mM NaCl; 70 µM Cobber(II)nitrate, pH 8.6, FVII polypeptide is eluted in a linear gradient from buffer E to buffer: 10 mM glycylglycine; 100 mM NaCl; 15 mM $CaCl_2$; 70 µM Cobber(II)nitrate, pH 8.6. The flow rate is 1 vol./hr.

Example 22

The Purification and Activation of FVII Polypeptide is Performed Through the Following Four Chromatographic Steps:

Step 1:
FVII polypeptide containing cell culture medium is adjusted to ion strength below 10 mS/cm by dilution and applied to a Q-Sepharose column pre-equilibrated with buffer A: 10 mM trihydroxymethylaminomethan (Tris); 150 mM NaCl pH 8.

After a washing step with 175 mM NaCl in the same buffer, FVII polypeptide is eluted by buffer B: 10 mM Tris; 150 mM NaCl; 25 mM $CaCl_2$ pH 8.

Step 2:
The eluate solution containing 104 mg/l FVII polypeptide is adjusted to a final composition: 10 mM Tris; 1M NaCl; 25 mM $CaCl_2$; 70 µM Cobber(II)nitrate pH 7.5 and applied to a Sepharose column with immobilized anti-FVII monoclonal antibody.

The antibody column is pre-equilibrated with buffer C: 10 mM Tris; 100 mM NaCl; 20 mM $CaCl_2$; 70 µM Cobber(II) nitrate pH 7.5. The column is then washed with 10 mM Tris; 2 M NaCl; 20 mM $CaCl_2$; 70 µM Cobber(II)nitrate pH 7.5 followed by buffer C. Thereafter FVII polypeptide is eluted by applying a buffer: 75 mM Tris; 30 mM trisodiumcitrate; 70 µM Cobber(II)nitrate pH 7.5.

Step 3:
The eluate is immediatly applied to a Q-Sepharose column pre-equilibrated with buffer: 10 mM Tris; 150 mM NaCl; 70 µM Cobber(II)nitrate pH 8.6.

The column is washed with the same buffer and FVII polypeptide is eluted in a linear gradient from buffer A to buffer D: 10 mM Tris; 500 mM NaCl; 70 µM Cobber(II) nitrate pH 8.6.

Step 4:
The fraction containing FVII polypeptide is adjusted to 2 mM ethylenediaminetetraacetic acid (EDTA) and ion strength below 10 mS/cm by dilution and immidiatly applied to a Q-Sepharose column pre-equilibrated with buffer: 10 mM glycylglycine; 150 mM NaCl pH 8.6.

After washing with buffer: 10 mM glycylglycine; 175 mM NaCl pH 8.6. and buffer E: 10 mM glycylglycine; 100 mM NaCl pH 8.6, FVII polypeptide is eluted in a linear gradient from buffer E to buffer: 10 mM glycylglycine; 100 mM NaCl; 15 mM $CaCl_2$ pH 8.6. The flow rate is 1 vol./hr.

Example 23

The purification and Activation of FVII Polypeptide is Performed Through the Following Four Chromatographic Steps.

Step 1:
FVII polypeptide containing cell culture medium is adjusted to ion strength below 10 mS/cm by dilution and applied to a Q-Sepharose column pre-equilibrated with buffer A: 10 mM trihydroxymethylaminomethan (Tris); 150 mM NaCl pH 8.

After a washing step with 175 mM NaCl in the same buffer FVII polypeptide is eluted by buffer B: 10 mM Tris; 150 mM NaCl; 25 mM $CaCl_2$ pH 8.

Step 2:

The eluate solution containing 104 mg/l FVII polypeptide is adjusted to a final composition: 10 mM Tris; 1M NaCl; 25 mM $CaCl_2$; 70 µM Cobber(II)nitrate pH 7.5 and applied to a Sepharose column with immobilized anti-FVII monoclonal antibody.

The antibody column is pre equilibrated with buffer C: 10 mM Tris; 100 mM NaCl; 20 mM $CaCl_2$; 70 µM Cobber(II)nitrate pH 7.5. The column is then washed with 10 mM Tris; 2 M NaCl; 20 mM $CaCl_2$; 70 µM Cobber(II)nitrate pH 7.5 followed by buffer C. Thereafter FVII polypeptide is eluted by applying a buffer: 75 mM Tris; 30 mM trisodiumcitrate; 70 µM Cobber(II)nitrate pH 7.5.

Step 3:

The eluate is adjusted to 2 mM EDTA and immediately applied to a Q-Sepharose column pre-equilibrated with buffer: 10 mM Tris; 150 mM NaCl pH 8.6.

The column is washed with the same buffer and FVII polypeptide is eluted in a linear gradient from buffer A to buffer D: 10 mM Tris; 500 mM NaCl pH 8.6.

Step 4:

The fraction containing FVII polypeptide is adjusted to ion strength below 10 mS/cm by dilution and immediately applied to a Q-Sepharose column pre-equilibrated with buffer: 10 mM glycylglycine; 150 mM NaCl pH 8.6.

After washing with buffer: 10 mM glycylglycine; 175 mM NaCl pH 8.6. and buffer E: 10 mM glycylglycine; 100 mM NaCl pH 8.6, FVII polypeptide is eluted in a linear gradient from buffer E to buffer: 10 mM glycylglycine; 100 mM NaCl; 15 mM $CaCl_2$ pH 8.6. The flow rate is 1 vol./hr.

Example 24

Ultra- and Diafiltration of Factor VII Polypeptides.

130 litres of CHO cell culture supernatant containing Factor VII polypeptide was harvested. The harvest was stabilized by addition histidine to 10 mM, adjusted to pH 6.0 and 1 mM $CaCl_2$ was added. The supernatant was filtered on a filter train encompassing 3.0 µm, 1.0 µm and 0.3 µm Millipore clarigard filters. The clarified supernatant was ultrafiltered across 0.2 m of Millipore Biomax 50 membrane until a 10× volume reduction. The ultrafiltration was carried out using a TMP setpoint of 32 psi and a crossflow setpoint of 600 ml/min. After reaching the desired retentate volume, 3 volume turnovers of diafiltration was done. The diafiltration buffer consisted of 5 mM histidine, 20 mM NaCl, 1 mM $CaCl_2$, 0.07 g/l Tween 80, pH 6.0.

Ultra and Diafiltration of wt-FVIIa 100 litres of CHO cell culture supernatant containing human wild type FVIIa is harvested and stabilized by addition of histidine to a concentration of 10 mM, adjusted to pH 6.0 and added 1 mM $CaCl_2$. The supernatant is filtered and ultrafiltered across $0.2\ m^2$ of Millipore Biomax 50 membrane until a 10× volume reduction. When the desired retentate volume is reached, 3 volume turnovers of diafiltration is performed. The diafiltration buffer consists of 5 mM histidine, 20 mM NaCl, 1 mM $CaCl_2$, 0.07 g/l Tween 80, pH 6.0.

---

The invention claimed is:

1. A method for the purification of a gamma-carboxyglutamic (GLA)-residue containing serine protease, said method comprising subjecting a solution comprising the protease to one or more purification steps, wherein (i) the GLA-residue containing serine protease is a human Factor VII polypeptide variant wherein the ratio between the activity of the Factor VII polypeptide variant and the activity of wild type human Factor VIIa (SEQ ID NO: 1) is at least about 1.25 when tested in an in vitro hydrolysis assay; and (ii) the pH to which the protease is subjected during at least one of the purification steps has a value between 4.5 and 6.9 or has a value between 8.8 and 9.8.

2. The method according to claim 1, wherein at least one of the purification steps is performed using a free calcium ion concentration higher than 1.2 mM.

3. The method according to claim 2, wherein the free calcium ion concentration in at least one of the purification steps is higher than 2.0 mM.

4. The method according to claim 1, wherein the free calcium ion concentration in at least one of the purification steps is lower than 0.10 mM.

5. The method according claim 4, wherein the free calcium ion concentration in at least one of the purification steps is lower than 0.05 mM.

6. The method according to claim 1, wherein, at least one of the purification steps is performed using a free ion concentration of a divalent metal cation other than a zinc ion and a calcium ion higher than 0.025 mM.

7. The method according to claim 6, wherein the divalent metal cation is selected from the list consisting of $Mg^{2+}$, $Cu^{2+}$, $Mn^{2+}$, $Co^{2+}$, $Fe^{2+}$, $Sm^{2+}$, $Ni^{2+}$, $Cd^{2+}$, $Hg^{2+}$ and $Sm^{2+}$.

8. The method according to claim 6, wherein the free ion concentration of a divalent metal cation other than a zinc ion and a calcium ion is higher than 0.1 mM.

9. The method according to claim 1, wherein the GLA-residue containing serine protease is purified in at least one of the purification steps in the presence of a divalent metal ion chelator.

10. The method according to claim 1, wherein the GLA-residue containing serine protease is purified at a pH between 4.5 and 6.9.

11. The method according to claim 1, wherein the GLA-residue containing serine protease is purified at a pH between 8.8 and 9.8.

12. The method according to claim 1, wherein said Factor VII polypeptide is a variant of wild-type human Factor VII (SEQ ID NO: 1) selected from the group consisting of: L305V-FVII, L305V/M306D/D309S-FVII, L305I-FVII, V158T/M298Q-FVII, V158D/E296 V/M298Q-F VII, K337A-FVII, M298Q-F VII, V158D/M298Q-FVII, L305V/K337A-FVII, V158D/E296V/M298Q/L305V-FVII, V158D/E296 V/M298Q/K33 7A-FVII, V158D/E296V/M298Q/L305V/K337A-FVII, E296 V-F VII, E296 V/M298Q-F VII, L305V/K337A-FVII, L305V/V158D-FVII, L305V/E296V-FVII, L305V/M298Q-FVII, L305V/V 1 58T-FVII, L305V/K337A/V158T-F VII, L305V/K337A/M298Q-F VII, L305 V/K337A/E296 V-FVII, L305V/K337A/V158D-F VII, L305V/V158D/M298Q-F VII, L305 V/V158D/E296 V-FVII, L305V/V158T/M298Q-FVII, L305 V/V158T/E296 V-FVII, L305V/E296V/M298Q-FVII, L305V/V158D/E296V/M298Q-FVII, L305V/V158T/E296V/M298Q-FVII, L305V/V158T/K337A/M298Q-F VII,L305V/V158T/E296V/K337A-FVII, L305V/V158D/K337A/M298Q-F VII,L305V/V158D/E296V/K337A-FVII, L305V/V158D/E296V/M298Q/K337A-FVII,L305V/V158T/E296V/M298Q/K337A-FVII, S314E/K316H-FVII, S314E/K316Q-FVII,S314E/L305V-FVII, S314E/K337A-FVII, S314E/E296V-FVII, S314E/M298Q-FVII, S314E/L305V/K337A-FVII, S314E/L305V/M298Q-FVII, S314E/L305V/K337A/M298Q-FVII, S314E/L305V/K337A/E296 V-FVII, S314E/L305V/E296V/M298Q-FVII, S314E/L305V/V158D/E296 V/M298Q-FVII, S314E/L305V/V158T/E296V/M298Q-FVII, S314E/L305V/V158T/K337A/M298Q-FVII, S314E/L305V/V158T/E296V/K337A-FVII, S314E/L305V/V158D/K337A/M298Q-FVII, S314E/L305V/V158D/E296V/K337A-FVII, S314E/L305V/V158D/E296V/M298Q/K337A-FVII, S314E/L305V/V158T/E296V/M298Q/K337A-FVII, F374Y/L305 V-FVII, F374Y/L305V/K337A-FVII, F374Y/L305V/314E-FVII, F374Y/K337A/314E-FVII, F374Y/L305V/K337A/S314E-FVII, F374Y/L305V/M298Q/K337A/S314E-FVII, and F374Y/L305V/E296V/M298Q/K337A/V158T/S314E.

* * * * *